US007608266B2

(12) United States Patent
Nilles et al.

(10) Patent No.: US 7,608,266 B2
(45) Date of Patent: Oct. 27, 2009

(54) YERSINIA SPECIES COMPOSITIONS

(75) Inventors: Matthew L. Nilles, Grand Forks, ND (US); Jyl S. Matson, Ann Arbor, MI (US)

(73) Assignee: University of North Dakota, Grand Forks, ND (US)

( * ) Notice: Subject to any disclaimer, the term of this patent is extended or adjusted under 35 U.S.C. 154(b) by 0 days.

(21) Appl. No.: 11/866,474

(22) Filed: Oct. 3, 2007

(65) Prior Publication Data

US 2008/0025999 A1 Jan. 31, 2008

Related U.S. Application Data

(63) Continuation of application No. 10/622,220, filed on Jul. 18, 2003, now Pat. No. 7,344,718.

(60) Provisional application No. 60/444,076, filed on Jan. 31, 2003.

(51) Int. Cl.
*A61K 39/00* (2006.01)
*A61K 39/02* (2006.01)

(52) U.S. Cl. ............... 424/185.1; 424/190.1; 424/234.1

(58) Field of Classification Search ............... 424/184.1
See application file for complete search history.

(56) References Cited

U.S. PATENT DOCUMENTS 4,879,213 A * 11/1989 Fox et al. ....................... 435/5
5,985,285 A 11/1999 Titball et al.
6,261,561 B1 7/2001 Stewart et al.

FOREIGN PATENT DOCUMENTS

WO WO 95/18231 7/1995
WO WO 96/28551 9/1996
WO WO 98/24912 A 6/1998
WO WO 02/077249 10/2002

OTHER PUBLICATIONS

Perry et al (Infection and Immunity vol. 66, No. 10, pp. 4611-4623, Oct. 1998).*

#PCT International Search Report, PCT/US04/02852, dated Apr. 7, 2005.

#Michiels et al., Analysis of virC, an Operon Involved in the Secretion of Yop Proteins by *Yersinia entercolitica*, Journal of Bacteriology, Aug. 1991, pp. 4994-5009, vol. 173, No. 16.

#Hu et al., Structural Organization of Virulence-Associated Plasmids of *Yersinia pestis*, Journal of Bacteriology, Oct. 1998, pp. 5192-5202, vol. 180, No. 19.

#Supplementary Partial European Search Report, EP 04 74 9309, dated Mar. 29, 2007.

#8th International Symposium on Yersinia, Sep. 4-8, 2002. Turku, Finland.

#Benner et al., Immune Response to Yersinia Outer Proteins and Other *Yersinia pestis* Antigens After Experimental Plague Infection in Mice, Infection and Immunity, Apr. 1999, pp. 1922-1928, vol. 67, No. 4.

#Edqvist et al., YscP and YscU Regulate Substrate Specificity of the Yersinia Type III Secretion System, Journal of Bacteriology, Apr. 2003, pp. 2259-2266, vol. 185, No. 7.

#Hoiczyk et al., Polymerization of a single protein of the pathogen *Yersinia enterocolitica* into needles punctures eukaryotic cells, PNAS, Apr. 10, 2001, pp. 4669-4674, vol. 98, No. 8.

#Titball et al., Vaccination against bubonic and pneumonic plague, Vaccine, 2001, pp. 4175-4184, vol. 19.

#Williamson, E.D., Plague vaccine research and development, Journal of Applied Microbiology, 2001, pp. 606-608, vol. 91.

#Wilson et al., Role of EscF, a putative needle complex protein, in the type III protein translocation system of enteropathogenic *Escherichia coli*, Cellular Microbiology, 2001, pp. 753-762, vol. 3, No. 11.

#Plotkin et al, Vaccines, 1988, p. 571, W.B. Saunders Co.

Cole et al., A plague o' both your hosts, Nature, Oct. 2001, pp. 467-470, vol. 413.

Parkhill et al., Genome sequence of *Yersinia pestis*, the causative agent of plague, Nature, Oct. 4, 2001, pp. 523-527, vol. 413.

Oyston et al., Yersinia: an update, Dec. 2002, <http://tim.trends.com>, pp. 550-551, vol. 10, No. 12.

Hill et al., Immunological characterisation of sub-units of the Yersinia type III secretion apparatus, Abstract at the 8th International Symposium on Yersinia, Sep. 4-8, 2002, Turku, Finland.

* cited by examiner

*Primary Examiner*—Mark Navarro
(74) *Attorney, Agent, or Firm*—TraskBritt

(57) ABSTRACT

A method of protecting an animal from infections with pathogens originating from *Yersinia* comprising administering an isolated or recombinant YscF protein to the animal is disclosed. The isolated or recombinant YscF protein may be administered as a vaccine. An isolated or recombinant YscF protein capable of conferring protection to an animal against a pathogen of a *Yersinia* origin is further disclosed. Nucleic acid molecules encoding the isolated or recombinant YscF protein are also disclosed. In other embodiments, antibodies generated against the isolated or recombinant YscF protein capable of conferring protection to an animal against a pathogen or a *Yersinia* origin and uses of the antibodies are described.

18 Claims, 5 Drawing Sheets

FIG. 1

```
                                   1                                                50
                Ht-YscF      (1)  MSNFSGFTKGTDIADLDAVAQTLKKPADDANKAVNDSIAALKDKPDNPAL
     YscF - Y pestis KIM5    (1)  MSNFSGFTKGTDIADLDAVAQTLKKPADDANKAVNDSIAALKDKPDNPAL
    YscF - Y. pestis CO92    (1)  MSNFSGFTKGTDIADLDAVAQTLKKPADDANKAVNDSIAALKDKPDNPAL
YscF - Y. enterocolitica     (1)  MSNFSGFAKGTDITDLDAVAQTLKKPADDANKAVNDSIAALKDTPDNPAL
               Consensus     (1)  MSNFSGFTKGTDIADLDAVAQTLKKPADDANKAVNDSIAALKDKPDNPAL
                                  51                                           95
                Ht-YscF     (51)  LADLQHSINKWSVIYNINSTIVRSMKDLMQGILQKFPLEHHHHHH (SEQ ID NO:12)
     YscF - Y pestis KIM5   (51)  LADLQHSINKWSVIYNINSTIVRSMKDLMQGILQKFP-------- (SEQ ID NO:17)
    YscF - Y. pestis CO92   (51)  LADLQHSINKWSVIYNINSTIVRSMKDLMQGILQKFP-------- (SEQ ID NO:18)
YscF - Y. enterocolitica    (51)  LADLQHSINKWSVIYNMSSTIVRSMKDLMQGILQKFP-------- (SEQ ID NO:4)
               Consensus    (51)  LADLQHSINKWSVIYNINSTIVRSMKDLMQGILQKFP (SEQ ID NO:19)
```

YERSINIA SPECIES COMPOSITIONS

CROSS-REFERENCE TO RELATED APPLICATIONS

This application is a continuation of U.S. patent application Ser. No. 10/622,220, filed Jul. 18, 2003, now U.S. Pat. No.7,344,718, which application claimed the benefit of U.S. Provisional Application 60/444,076, Filed Jan. 31, 2003, pursuant to 35 U.S.C. § 119(e). The disclosure of each of the above-identified applications is hereby incorporated herein by this reference in its entirety.

TECHNICAL FIELD

The invention relates generally to the field of biotechnology and, more particularly, to compositions for eliciting an immune response including an isolated or recombinant YscF or an epitope thereof that provides protection against infections caused by members of the genus *Yersinia.*

BACKGROUND

*Yersinia pestis* causes a rapidly progressing disease in humans with a high mortality rate. Due to the severe nature of the disease and its ability for aerosol transmission, a better vaccine for the disease caused by *Y. pestis*, "the plague," is desirable. Current efforts for vaccine development have focused on two proteins: LcrV and the F1 antigen.[25] The best results to date have been obtained by using a combination of recombinant LcrV and F1 subunits.[25] This vaccine demonstrates protection against both pneumonic and systemic forms of plague.[25] One of the potential limitations of this vaccine is that the F1 antigen is not required for full virulence of *Y. pestis* as F1-negative strains have the same $L_{50}$ value as F1-positive strains.[6-8,27] While the recombinant subunit vaccine is effective and offers protection against F1 minus strains of *Y. pestis*, the inclusion of other antigens with the LcrV-F1 vaccine could improve the ability of the resulting vaccine to offer protection against multiple *Y. pestis* strains, or new antigens could be developed as separate vaccine candidates. Another *Yersinia* protein that has been shown to provide some protection is YopD.[25]

The type III secretion apparatus is encoded on the low-calcium response (LCR) virulence plasmid, pCD1 in strain KIM[20] of *Y. pestis*. The type III secretion apparatus is a conserved virulence mechanism that is absolutely required for virulence of *Y. pestis*.[19] YscF (see, SEQ ID NOS:1 and 2 for the amino acid sequence and the YscF sequence, respectively) is a surface-localized protein that is required both to secrete Yops and to translocate toxins into eukaryotic cells.[1,10, 12] The type III secretion apparatus and YscF are also encoded for by the virulence plasmids of *Yersinia pseudotuberculosis* and *Yersinia enterocolitica. Y. pseudotuberculosis* and *Y. enterocolitica* are enteropathogenic bacteria transmitted by the oral route and cause a range of gastrointestinal diseases collectively referred to as "yersiniosis." The nucleic acid sequence for YscF of *Y. pseudotuberculosis* and the amino acid sequence for YscF of *Y. pseudotuberculosis* are substantially similar to the yscF gene and YscF protein of *Y. pestis* based on homologies and comparisons of other proteins of the type III secretion complex. The nucleic acid sequence encoding YscF of *Y. enterocolitica* includes SEQ ID NO:3 and the amino acid sequence contains SEQ ID NO:4. An alignment of the YscF proteins from these organisms is illustrated in FIG. 1.

One report speculates that YscF polymerization is required for a YscF needle to puncture eukaryotic cell membranes.[12] Other researchers suggest that YscF and its homologs function to provide a base that a translocon complex is built upon, or that YscF builds a conduit from the bacterium to the eukaryotic membrane.[4] This suggestion seems more likely given that other proteins such as YopB, YopD, and LcrV are also required for translocation into eukaryotic cells.[9, 11, 13, 17, 18, 21, 23, 24] However, the exact function of YscF remains unknown.

Other pathogenesis-related type III secretion systems possess homologs to YscF. In pathogenic *Salmonella* and *Shigella*, the YscF homologs (PrgI (see, SEQ ID NOS:5 and 6 for the amino acid sequence and nucleic acid sequences, respectively) and MxiH, respectively (see, SEQ ID NOS:7 and 8 for the amino acid sequence and nucleic acid sequence, respectively)) have been demonstrated to form a needle structure that protrudes from the surface of bacterial cells.[2, 15, 16] The best characterized homolog of YscF is EscF (see, SEQ ID NOS:9 and 10 for the amino acid sequence and nucleic acid sequence, respectively) of enteropathogenic *E. coli* (EPEC). EscF is required for "attaching and effacing" (A/E) lesion formation on the intestinal mucosa and for type III secretion of effector proteins.[5,22,29] EscF is thought to be a structural component of the needle complex on the bacterial surface as it binds EspA, the major component of a filamentous surface organelle, and is required for formation of the EspA filaments.[5, 22, 29] However, this surface localization has never been directly visualized and the only EscF antiserum generated was unable to recognize the native protein.[29]

Based on the fact that YscF is thought to be a surface-expressed protein in the pathogens of *Yersinia* and is required for virulence, it was determined whether YscF could serve as a protective antigen against experimental infection with pathogens of *Yersinia.*

SUMMARY OF THE INVENTION

In one exemplary embodiment, a composition of matter comprising YscF of a *Yersinia* origin is disclosed. The composition of matter may comprise isolated or recombinant YscF; a recombinant vector including the nucleic acid associated with isolated or recombinant YscF; synthetic YscF; a nucleic acid encoding the isolated or recombinant YscF; a recombinant nucleic acid which comprises a nucleotide sequence originating from the genome of *Yersinia*; a polypeptide having an amino acid sequence originating from a protein of *Yersinia*, the polypeptide being produced by a cell capable of producing it due to genetic engineering with appropriate recombinant DNA; an isolated or synthetic antibody which specifically recognizes a part or epitope of the isolated or recombinant YscF; or a recombinant vector which contains nucleic acid comprising a nucleotide sequence coding for a protein or antigenic peptide associated with isolated or recombinant YscF.

In another exemplary embodiment, a recombinant nucleic acid, more specifically recombinant DNA, which comprises a nucleotide sequence encoding for isolated or recombinant YscF, as shown in SEQ ID NO:11, is disclosed (see, SEQ ID NO:12 for the amino acid sequence encoded by SEQ ID NO:11). In a further embodiment, a pharmaceutical composition including the nucleotide sequence encoding for isolated or recombinant YscF is disclosed. Use of the recombinant nucleic acid encoding the isolated or recombinant YscF for the prophylaxis of an animal is also disclosed.

In an additional embodiment, a peptide comprising an isolated or recombinant YscF amino acid sequence is disclosed. The YscF proteins disclosed herein are capable of conferring protection to an animal against a pathogen of *Yersinia* origin. In a further embodiment, a pharmaceutical composition including the isolated or recombinant YscF is disclosed. Use of the isolated or recombinant YscF for the prophylaxis of an animal is also disclosed.

In yet another embodiment, a vaccine for vaccinating animals, in particular mammals, to protect them against infections caused by pathogens of *Yersinia* origin, such as *Y. pestis, Y. pseudotuberculosis* and *Y. enterocolitica* is disclosed. The vaccine comprises isolated or recombinant YscF; a recombinant vector which contains the nucleic acid coding for a protein or antigenic peptide associated with isolated or recombinant YscF; an antigenic part or epitope of isolated or recombinant YscF; or a peptide mimicking an antigenic component of isolated or recombinant YscF; together with a suitable carrier or adjuvant.

Use of a composition comprising an isolated or recombinant YscF for the manufacture of a medicament for the treatment of a mammal infected with a *Yersinia* pathogen, such as *Y. pestis, Y. pseudotuberculosis* or *Y. enterocolitica*, is further disclosed. In a further aspect, the invention discloses the use of a composition comprising antibodies or fragments thereof that bind to isolated or recombinant YscF for the manufacture of a medicament for the treatment of a mammal infected with a *Yersinia* pathogen, such as *Y. pestis, Y. pseudotuberculosis* or *Y. enterocolitica* or prevention of such an infection.

In a further exemplary embodiment, a diagnostic kit for detecting antibodies generated against isolated or recombinant YscF in a sample, in particular a biological sample such as blood or blood serum, sputum, saliva, or tissue (i.e. lymph nodes), originating from an animal, in particular a mammal, is disclosed. The diagnostic kit comprises an antibody or fragment thereof that binds to the isolated or recombinant YscF or a fragment thereof and suitable detection means of an antibody detection assay.

The invention also discloses a diagnostic kit for detecting an antigen or epitope originating from YscF in a sample, in particular a biological sample such as blood or blood serum, sputum, saliva, or tissue, derived from an animal, in particular a mammal, comprising an antibody or fragment thereof that recognizes a part or epitope of YscF, and suitable detection means of an antigen detection assay.

In a further embodiment, a process for diagnosing whether an animal, in particular a mammal, is carrying the antibodies directed against isolated or recombinant YscF is disclosed. The process comprises preparing a sample, in particular a biological sample such as blood or blood serum, sputum, saliva, or tissue, derived from the animal, and examining whether the biological sample contains the isolated or recombinant YscF antigen, or an antibody specifically recognizing the isolated or recombinant YscF, the YscF being associated with infections caused by bacteria of the *Yersinia* species.

A method for vaccinating a mammal comprising cloning a nucleic acid sequence encoding an isolated or recombinant YscF of a *Yersinia* origin or a homolog thereof into an expression vector is disclosed in another embodiment. The method further includes inducing the expression of the nucleic acid and collecting the isolated or recombinant YscF or homologs thereof. The isolated or recombinant YscF or homolog thereof is administered to an animal, such as a mammal, to generate an immune response against the isolated or recombinant YscF or homolog thereof.

A process for manufacturing a composition for use in vaccinating animals is also disclosed. The process comprises cloning a nucleic acid sequence encoding an isolated or recombinant YscF or a homolog thereof into an expression vector. The process further includes inducing the expression of the nucleic acid and collecting the isolated or recombinant YscF. The isolated or recombinant YscF or homolog thereof is mixed with a pharmaceutically acceptable excipient to produce the composition.

In an additional embodiment, a method for generating an immune response is disclosed. The method includes cloning a nucleic acid sequence encoding an isolated or recombinant YscF or a homolog thereof into an expression vector. The method further includes inducing the expression of the nucleic acid and collecting the isolated or recombinant YscF or homolog thereof. The isolated or recombinant YscF or homolog thereof is administered to a subject to generate the immune response in the subject.

A method of collecting antibodies generated against an epitope of an isolated or recombinant YscF or homolog thereof is disclosed in a further embodiment. The method includes cloning a nucleic acid sequence encoding the isolated or recombinant YscF or a homolog thereof into an expression vector. The method further includes inducing the expression of the nucleic acid and collecting the isolated or recombinant YscF or homolog thereof. The isolated or recombinant YscF or homolog thereof is administered to a subject. The isolated or recombinant YscF or a homolog thereof is immobilized on a substrate and serum collected from the subject is added to the substrate such that antibodies in the serum directed against the isolated or recombinant YscF or a homolog thereof adhere to the immobilized protein.

In an additional embodiment, a peptide corresponding to an epitope of the isolated or recombinant YscF or homolog thereof to which an antibody binds is disclosed. A composition or vaccine including the epitope of the isolated or recombinant YscF or homolog thereof to which an antibody binds is further disclosed. The use of a composition comprising the epitope of the isolated or recombinant YscF or homolog thereof to which an antibody binds for the manufacture of a medicament for the treatment of a mammal infected with a pathogen of *Yersinia* origin, such as *Y. pestis, Y. pseudotuberculosis* or *Y. enterocolitica*, is further disclosed.

BRIEF DESCRIPTION OF THE DRAWINGS

FIG. 1 is a sequence alignment of peptide sequences of the YscF protein from various *Yersinia* bacteria including SEQ ID NOS:4, 13, 17, 18 and 19.

DETAILED DESCRIPTION OF THE INVENTION

Figure 2:
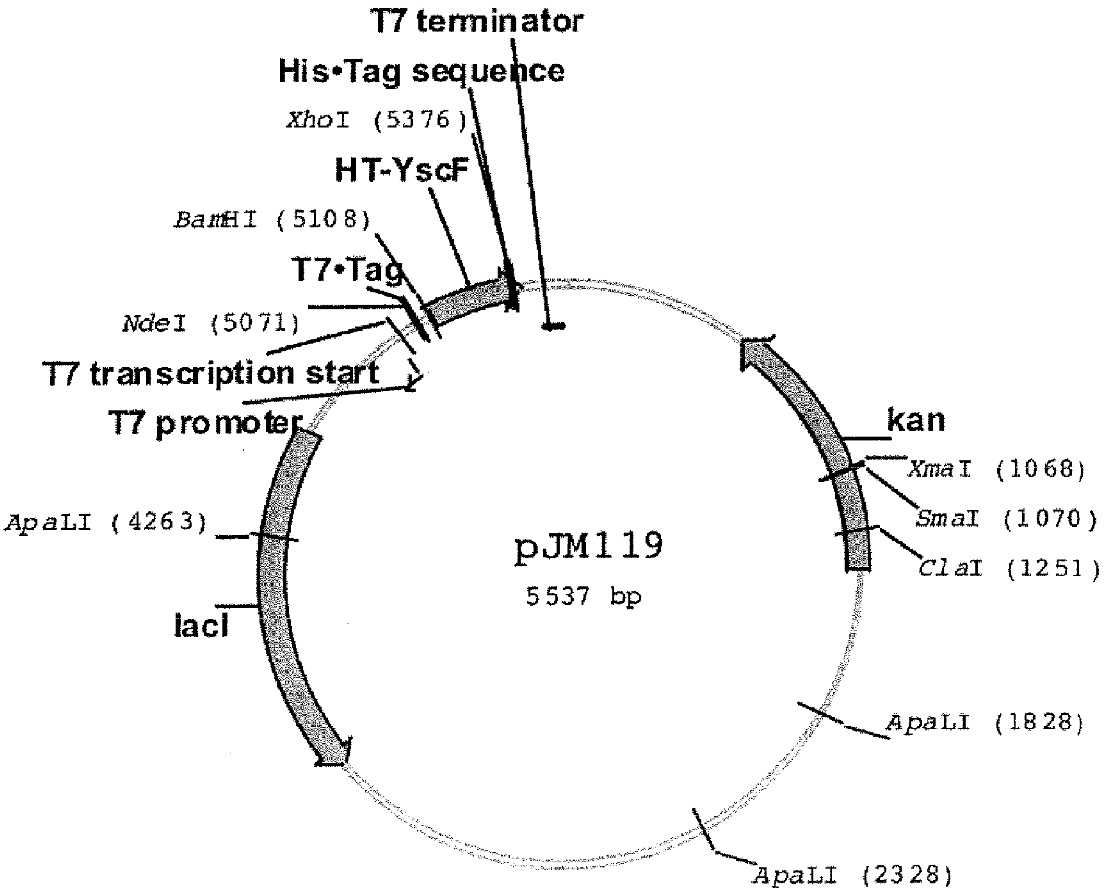
FIG. 2 is a map of the pJM119 plasmid (SEQ ID NO: 13).

The embodiments described herein disclose the successful immunization of mice with isolated or recombinant YscF. Previous attempts to immunize mice against subsequent challenge with *Y. pestis* have failed. For instance, Hill et al. immunized mice with YscF, but were not able to show protection in the mice against subsequent challenge with *Y. pestis*. (See, Hill et al., *Immunological characterization of subunits of the Yersinia type III secretion apparatus*, Abstract at the 8th International Symposium on *Yersinia*, Sep. 4-8, 2002, Turku, Finland.) Thus, the present invention discloses a surprising discovery that isolated or recombinant YscF is able to protect subjects against subsequent challenge with a pathogen of *Yersinia* origin. The immunization disclosed herein results in a high anti-YscF titer and protection against challenge with a pathogen of *Yersinia* origin. The embodiments described herein disclose that YscF provides protection against challenge with a pathogen of *Yersinia* origin and, thus, is a vaccine candidate. The isolated or recombinant YscF may also be used in conjunction with the other known plague antigens.

The phrase "suitable excipient" as used herein means that an active ingredient can be formulated, for example, with the conventional generally non-toxic, well-known pharmaceutically acceptable carriers (e.g., sterile water, saline solution and other acceptable carriers) for making suitable pharmaceutical compositions. The suitable excipient may also include adjuvants as described herein. A person of ordinary skill in the art will recognize that a suitable excipient, examples of which are provided herein, is an art-recognized term.

The vaccine may also comprise compounds including an adjuvant activity. Adjuvants are non-specific stimulators of the immune system and enhance the immune response of the animal host to the vaccine. Examples of adjuvants that may be used include, but are not limited to, incomplete Freund's adjuvant, Freunds Complete adjuvant, vitamin E, non-ionic block polymers, muramyldipeptides, ISCOMs (immune stimulating complexes), Saponins, mineral oil, vegetable oil, Carbopol, Alhydrogel, and Ribi. Adjuvants suitable for mucosal application include *E. coli* heat-labile toxin or *Cholera* toxin. Other suitable adjuvants include aluminum hydroxide, aluminum phosphate or aluminum oxide, oil-emulsions or vitamin-E solubilisate. The vaccine may also include preservatives to increase the shelf live of the vaccine.

In the exemplary embodiments herein, the vaccines or compositions including the isolated or recombinant YscF of *Yersinia* origin or homologs thereof may also include pharmaceutically acceptable carriers including, but not limited to, water, culture fluid in which the bacteria were cultured, a solution of physiological salt concentration, stabilizers such as SPGA, carbohydrates (e.g., sorbitol, mannitol, starch, sucrose, glucose, dextran), proteins such as albumin or casein, protein-containing agents such as bovine serum or skimmed milk, and buffers (e.g., phosphate buffer). When stabilizers are added to the vaccine, the vaccine is suitable for freeze-drying. Accordingly, in another exemplary embodiment, the vaccine may be in a freeze-dried form as is known by those of ordinary skill in the art.

The vaccines of the exemplary embodiments may be administered to humans or animals inter alia intraperitoneally, intranasally, intradermally, subcutaneously, orally, by aerosol or intramuscularly. As known in the art, the vaccine may be in a unit dosage form and provided in sterile form in a sealed container. The dosage administered to the animal will vary depending on the age, weight and animal vaccinated, as well as the mode of administration and the frequency of administrations employed. Regimens for inducing an immune response including dose and therapy may be guided by the initial response of the animal to the first vaccine dose and clinical judgment as known by those of ordinary skill in the art.

Types of animals that the vaccine may be administered to include any mammal, such as humans, pigs, mice, prairie dogs, cats, dogs and rats or other animals. The vaccine may be used to generate a "herd immunity" in a population or a subpopulation of animals. As known in the art, the phrase "herd immunity" refers to the effect achieved when enough individuals of the population or subpopulation are vaccinated such that the particular disease is not able to spread through the population or subpopulation. Thus, the immunized individuals are protected as are the non-immunized individuals since the disease cannot effectively spread through the population or subpopulation. Accordingly, the vaccine has utility in a public health program designed to help prevent the transmission of infections caused by pathogens of *Yersinia* origin.

The phrase "pathogens of *Yersinia* origin" will be used to refer to members of the genus *Yersinia* that cause disease including, but not limited to, *Y. pestis, Y. pseudotuberculosis* and *Y. enterocolitica* which encode substantially identical and functionally equivalent YscF proteins. As described herein, the term "YscF" will be used to refer to the YscF protein originating from any of *Y. pestis, Y. pseudotuberculosis*, and *Y. enterocolitica* unless otherwise specified. The YscF proteins of *Y. pestis* and *Y. enterocolitica* include substantially similar sequences as indicated in the alignment of FIG. 1. Further, since many proteins of the type III secretion complex of both *Y. pestis* and *Y. pseudotuberculosis* are substantially similar, YscF from *Y. pestis* and *Y. pseudotuberculosis* are considered to be substantially similar.

The term "protective" or "conferring protection" as used herein with reference to a protein will be used to refer to the ability of the protein to increase the lethal dose of pathogenic bacteria required to kill 50% of hosts infected with the pathogenic bacteria after administration of the protein to the host.

As used herein, the term "recombinant YscF" will be, used to refer to a YscF protein that includes amino acid residues in addition to or different than wild-type YscF. For instance, His-tagged YscF is a recombinant YscF (see, SEQ ID NOS:11 and 12 for the nucleic acid and amino acid sequences of His-tagged YscF, respectively).

In addition to the peptides, vaccines and compositions including isolated or recombinant YscF or homologs thereof described herein, peptides functionally and immunologically related to the isolated or recombinant YscF or homologs thereof that possess the same functions and immunologic properties as the isolated or recombinant YscF or analogs thereof are further disclosed. For instance, amino acid substitutions in the peptide may not substantially alter the biological and immunological activities of the protein and have been described, e.g., in Neurath et al. in "The Proteins" Academic Press, New York (1979). Amino acid replacements that occur frequently in evolution and do not alter the function or immunological activity of the protein include inter alia, Ser/Ala, Ser/Gly, Asp/Gly, Asp/Asn, Ile/Val (see, M. C. Dayhof, Atlas of protein sequence and structure, *Nat. Biomed. Res. Found.*, Washington D.C., 1978, vol. 5, suppl. 3). Other amino acid substitutions that often do not alter the function of immunogenicity of proteins include Asp/Glu, Thr/Ser, Ala/Sly, Ala/Thr, Ser/Asn/Ala/Val, Thr/Phe, Ala/Pro, Lys/Arg, Leu/Ile, Leu/Val and Ala/Glu. Based on this information, Lipman and Pearson have developed a method for rapid and sensitive protein comparison (*Science,* 227, 1435-1441, 1985) and determining the functional similarity between homologous proteins. Accordingly, amino acid substitutions which do not alter the function or immunological properties of the isolated or recombinant YscF or homologs thereof are encompassed by the present invention.

In addition to the nucleotide sequences, vaccines or compositions including the nucleotide sequences encoding for the isolated or recombinant YscF or homologs thereof, nucleotide sequences having functions substantially similar to the nucleotides encoding the isolated or recombinant YscF or homologs thereof are further disclosed. For instance, as known in the art, the degeneracy of the genetic code and the "wobble" hypothesis allows for nucleotide substitutions to occur and, yet, the altered nucleotide sequence encodes a protein having a function or immunogenicity substantially similar to the proteins encoded by the original nucleotide sequence since some amino acids are encoded by more than one codon.

Further, as previously described herein, some amino acid substitutions may not alter the function or immunological properties of the protein. For instance, single nucleotide polymorphisms, allelic variants, insertions and deletions may have different nucleotide sequences from those disclosed herein, but still encode isolated or recombinant YscF proteins or homologs thereof. Accordingly, nucleotide substitutions in the nucleic acids of the present invention which do not substantially alter the peptide sequence of the isolated or recombinant YscF proteins or homologs thereof and nucleotide substitutions which encode for proteins having substantially the same function or immunological properties as the isolated or recombinant YscF proteins or homologs thereof are encompassed by the present invention. Thus, nucleic acid sequences that hybridize to the nucleic acid sequences encoding the isolated or recombinant YscF or homologs thereof under highly stringent conditions, such as high salt conditions, are within the scope of the present invention.

EXAMPLE I

Expression and Purification of HT-YscF

Figure 3:
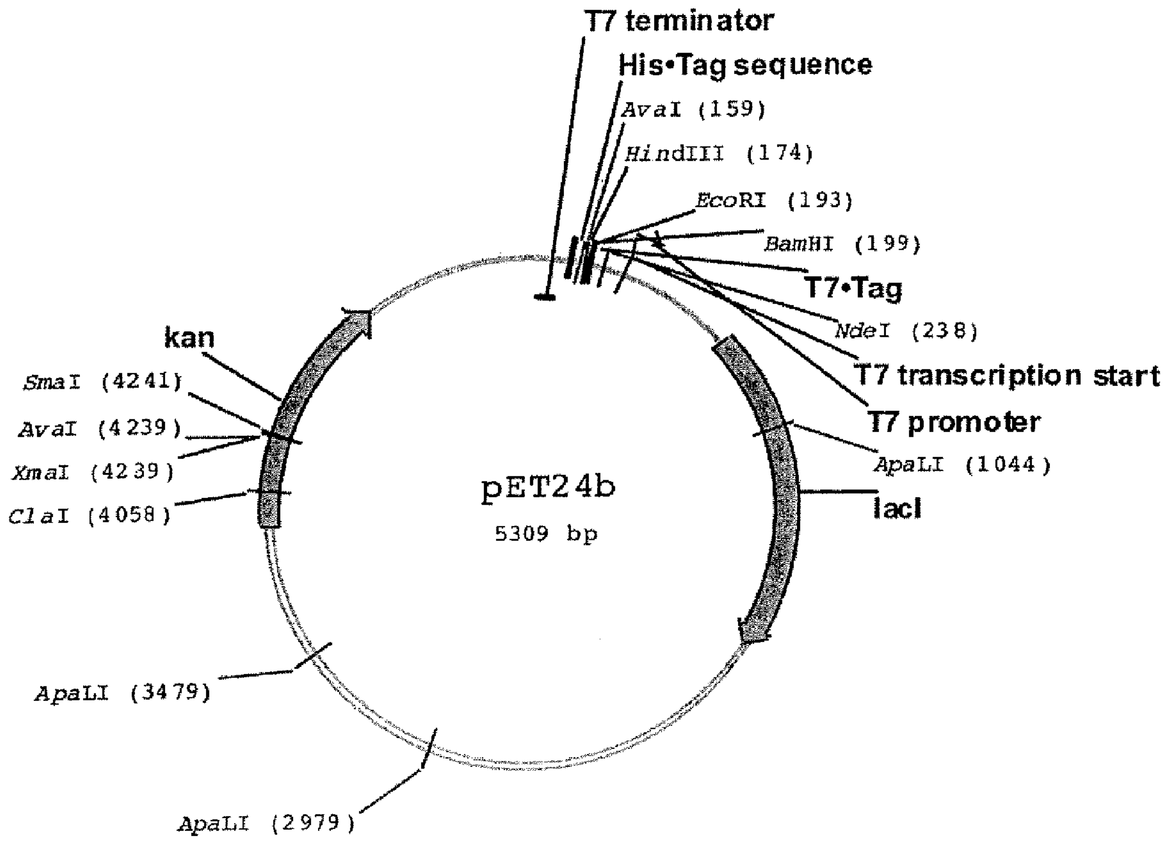
FIG. 3 is a map of the pET24b plasmid (SEQ ID NO: 14).

Expression and purification of IT-YscF. Plasmid pJM119 (see, FIG. 2 and SEQ ID NO:13) was constructed by cloning a BamHI- and XhoI-cleaved PCR product into pET24b (SEQ ID NO:14), a cloning vector commercially available from Novagen of Madison, Wis. (see, FIG. 3). The primers used to amplify yscF were HT-YscF Start (5' CGG GAT CCG ATG AGT AAC TTC TCT GGA TTT 3') (SEQ ID NO:15) and HT-YscF Stop (5' CCG CTC GAG TGG GAA CTT CTC TAG GAT GCC 3') (SEQ ID NO:16). *E. coli* BL21 (DE3) (commercially available from Novagen of Madison, Wis.) harboring pJM119 was grown in one liter of LB broth containing carbenicillin at 37° C. Expression of HT-YscF was induced after 2 hours of growth with 0.3 mM IPTG and incubated until the $A_{550}$ reached ~1.0.

Figure 4A:
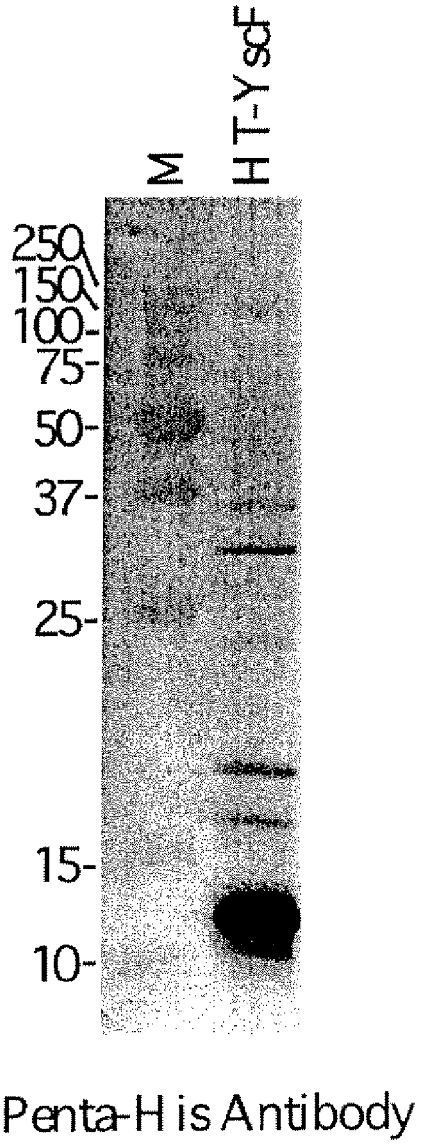
FIGS. 4A and 4B illustrate recovered His-tagged YscF protein run on an SDS-PAGE.
Figure 4B:
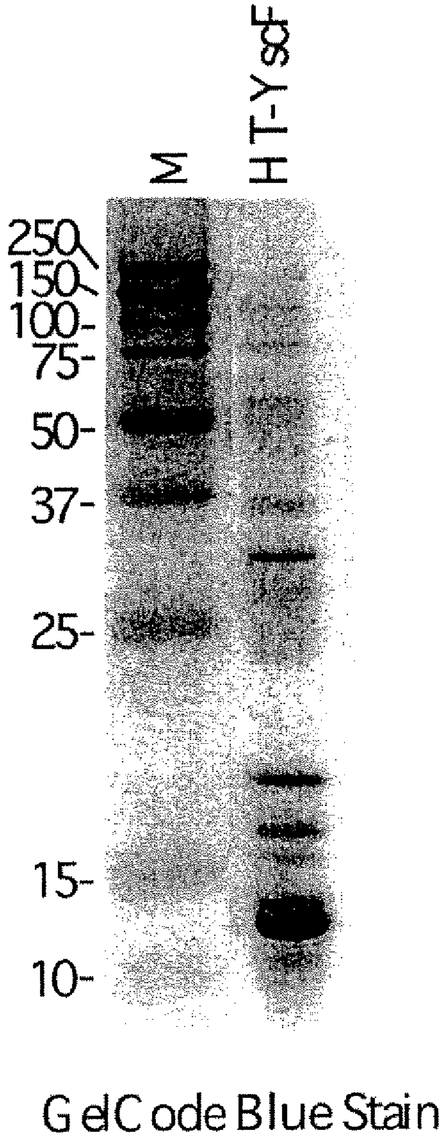

Cells were harvested by centrifugation and disintegrated by passage through a French pressure cell at 20,000 lb/in$^2$. Subsequent to disintegration, the extracts were clarified by centrifugation at 3200×g for 20 minutes at 4° C. Affinity purification of His-tagged YscF (HT-YscF) was performed using Talon resin (Clontech of Palo Alto, Calif.) as described by the manufacturer. Purity of the recovered protein was estimated by SDS-PAGE on a 15% (wt/vol) gel followed by staining with Gelcode Blue (Pierce of Rockford, Ill.). The purified protein ran as multiple bands on the gel. A band that corresponded to the predicted size of HT-YscF was the dominant species and other larger bands could also be visualized (see, FIGS. 4A and 4B). Based on the sizes of the larger bands and the fact that they are recognized by the penta-His antibodies, it is likely that the larger bands represent dimers and other multimers of YscF. This is not surprising as YscF and its homologs are known to form multimeric structures.

EXAMPLE II

The His-tag is removed from the isolated His-tagged YscF protein using known processes. For instance, treatment of the His-tagged YscF protein with Staphylococcal peptidase I (Protease V8), which is commercially available from Worthington Biochem of Lakewood, N.J., is performed. (See, J. J. Birktoft et al., *Glutamyl endopeptidases*, Methods of Enzymology (1994) 244:114126.) Cleavage of the His-tagged YscF with Staphylococcal peptidase I results in breaking of the peptide bond between amino acids 89 and 90 of the His-tagged YscF (SEQ ID NO:12), and results in the YscF (SEQ ID NO:1) with an additional two amino acids, leucine and glutamate, on the carboxyl terminus. Staphylococcal peptidase I is also referred to as glutamyl endopeptidase.

EXAMPLE III

In other exemplary embodiments, the nucleic acid sequences encoding YscF from *Y. enterocolitica* (SEQ ID NO:3) or *Y. pseudotuberculosis* or the homologs of YscF, i.e., the nucleic acids encoding PrgI, Mxih and EscF (SEQ ID NOS:6, 8 and 10), respectively, are cloned and expressed. In this manner, His-tagged YscF from *Y. enterocolitica* or *Y. pseudotuberculosis* or His-tagged PrgI, MxiH and EscF proteins are collected and mixed with a suitable excipient to form a pharmaceutical composition. The pharmaceutical composition is used to immunize mice.

EXAMPLE IV

Immunization Protocol

Active immunization of outbred mice followed by challenge with *Y. pestis* KIM5. KIM5 is a strain of *Y. pestis* that, when administered to a mammal, causes an infection in substantially the same manner as wild-type *Y. pestis*. For challenge with *Y. pestis,* 6- to 8-week-old female Swiss-Webster mice were immunized i.p. (intraperitoneally) with 40 μg/mouse His-tagged YscF or phosphate-buffered saline[3] PBS (control mice) emulsified 1:1 with complete Freund's adjuvant (CFA). Experimental mice were boosted with 40 μg/mouse His-tagged YscF in incomplete Freund's adjuvant (IFA) at two weeks and 20 μg/mouse His-tagged YscF in IFA at 4 weeks post-immunization. Negative control mice received PBS emulsified with IFA. Two weeks after the final immunization, groups of 10 mice were challenged i.v. (intravenously) via the retro-orbital sinus with $10^1$ to $10^6$ CFU (colony forming units) *Y. pestis* KIM5 in PBS. The mice were observed for 19 days after challenge, and the average doses required to kill 50% of the mice ($LD_{50}$) for the treatment groups were calculated using the extrapolation method of Reed and Muench.[26]

EXAMPLE V

The vaccine including the isolated or recombinant YscF is combined with other antigens protective against infections with bacteria, such as *Yersinia* bacteria, including LcrV, F1 antigen, YopD and a live attenuated *Yersinia* bacterium (EV76 strain), a live recombinant carrier bacterium including a nucleic acid encoding the isolated or recombinant YscF, an inactive or killed whole cell *Yersinia* bacterium and any combinations thereof. In a further embodiment, the vaccine including the isolated or recombinant YscF is combined with homologs of YscF including PrgI, MxiH, EscF and mixtures thereof.

EXAMPLE VI

In another exemplary embodiment, the nucleic acids encoding the isolated or recombinant YscF of *Yersinia* origin or homologs thereof are introduced into an animal through a microorganism (e.g., a bacterium or a virus) in such a way that the recombinant microorganism is able to replicate and, thus, express the polypeptide encoded by the nucleic acids and elicit an immune response in the infected animal. (See, M. A. Berry et al. in *Nature* (1995), 377, pp. 632-635, discloses the preparation of vaccines using nucleic acid molecules.)

The vaccines including the nucleic acid encoding the isolated or recombinant YscF or homologs thereof are manufactured by transforming an expression vector including the nucleic acid encoding the isolated or recombinant YscF or homologs thereof into a cell, multiplying the expression vectors and injecting purified expression vectors into a subject. As known by those of ordinary skill in the art, nucleic acid vaccines may comprise expressible DNA or mRNA which may be delivered to cells of the animal to be vaccinated. When the nucleic acid encoding the isolated or recombinant YscF or homologs thereof is operably linked to a promoter expressible in the animal to be vaccinated, the cells of the animal will express the nucleic acid and, thus, include the capability to induce a cell-mediated immune response, a humoral immune response or a combination thereof.

EXAMPLE VII

Mice that were immunized with YscF demonstrated a 134-fold increase in the calculated $LD_{50}$ value as compared to PBS-immunized mice (Table 1). The increased $LD_{50}$ value demonstrates that immunization with YscF protects mice from lethal challenge with *Y. pestis* KIM5 (Table 1). This result demonstrates that YscF can be developed as a novel vaccine for pathogens of *Yersinia* origin, such as *Y. pestis*, or could serve as another antigen in a multivalent *Yersinia* vaccine including YscF, the F1 antigen, LcrV, and combinations thereof. Based on the high degree of homology among YscF proteins originating from strains of *Y. pestis* and *Y. enterocolitica* as illustrated in FIG. 1, the protection conferred by YscF against *Y. pestis* is also expected to confer protection against infections with *Y. enterocolitica*, which includes a substantially similar type III secretion system. Further, since many proteins of the type III secretion complex of both *Y. pestis* and *Y. pseudotuberculosis* are substantially similar, the protection conferred by YscF against *Y. pestis* is also expected to confer protection against infections with *Y. pseudotuberculosis*.

TABLE 1

| Immunogen | anti-YscF GMT* | $LD_{50}$ | Fold increase in survival |
|---|---|---|---|
| PBS | <1:400 | 159 | — |
| HT-YscF | 1:40,000 | 21,344 | 134 |

*Geometric mean titer

EXAMPLE VIII

Characterization of the Antibody Response to HT-YscF

Characterization of the antibody response to HT-YscF. Flat-bottom, 96-well Nunc Maxisorp immunoplates (Fisher Scientific, Pittsburgh, Pa.) were coated with 100 µl of HT-YscF solution (4 µg/ml in Binding solution (0.1 M $NaH_2PO_4$, pH 9.0) at room temperature for 2 hours (or overnight at 4° C.)). The wells were blocked with 200 µl/well blocking buffer (1% bovine serum albumin in JIBS (tris-buffered saline[3]+ 0.5% Tween 20)) and washed with TTBS. Test sera were serially diluted in blocking buffer and 100 µl of each dilution was added to duplicate wells that were incubated for 2 hours at RT (or overnight at 4° C.). The plates were washed and incubated for 2 hours at RT with alkaline-phosphatase-conjugated anti-mouse secondary antibody. The high antibody response observed against HT-YscF is evidence that YscF is not only expressed during the course of an infection with pathogens of *Yersinia* origin, but also that YscF is in a location accessible to antibodies, such as on the bacterial surface.

For quantitation of YscF-specific immunoglobulin isotypes and subclasses, the plates were coated with alkaline-phosphatase-labeled anti-mouse isotype-specific antibody (1:400 in blocking buffer; Southern Biotech, Birmingham, Ala.). The wells were washed and 75 µl 3 mM para-nitro phenyl phosphate (p-NPP) was added to each well. The plates were incubated for 15 minutes at RT (room temperature) and the reaction was stopped by the addition of 50 µl of 1.5 M NaOH to each well. $A_{405}$ was measured with a Thermo Max kinetic microplate reader (Molecular Devices Corp., Menlo Park, Calif.) to monitor the cleavage of p-NPP. Antibody titers were determined as reciprocal numbers of the highest serum dilution that displayed values for optical density two-fold higher than the value of the control serum.

Anti-YscF antibody titers were determined two weeks following the last immunization, prior to challenge. The YscF-specific antibody titers of PBS-immunized mice were below the ELISA assay baseline of 400 (Table 1), as was the pre-immune serum (data not shown). However, the HT-YscF immunized mice reached a GMT (geometric mean titer) of 40,000 (Table 1). The IgG titer was very highs especially the IgG1 and IgG2b subclasses, and the antibody response consisted primarily of antibodies possessing kappa light chains. Interestingly, Titball et al. showed that IgG1 titers to the F1-LcrV chimera correlated very well with protection against pneumonic plague.[28] This suggests that YscF may afford protection against pneumonic challenge as well as against systemic challenge.

EXAMPLE IX

Derivatives of *Y. pestis* KIM8-3002 (KIM5 pPCP1-minus, $Sm^r$) were grown in a chemically defined medium[17] at 26° C. for 2 hours in the presence (lanes 1, 3, and 5) (FIG. 5) or absence of calcium (lanes 2, 4, and 6) (FIG. 5) or the presence of arabinose (lanes 3 and 4) (FIG. 5). pPCP1 is a plasmid originating from *Y. pestis* and has the Medline Accession No. AL109969 (see, Parkhill et al., Genome sequence of *Yersinia pestis*, the causative agent of the plague, *Nature* 413 (6855), 523-527 (2001)). Lanes 1 and 2 contain *Y. pestis* KIM8-3002. Lanes 3 and 4 contain *Y. pestis* KIM8-3002 expressing YscF from pBAD18-YscF (SEQ ID NO:20). Lanes 5 and 6 contain *Y. pestis* KIM8-3002 harboring a deletion in the yscF gene. After the 2 hours growth, the culture was shifted to 37° C. to induce expression of the YscF-type III secretion system and the Low Calcium Response. Following 4 hours of growth at 37° C., cultures were centrifuged to obtain whole cell fractions and cell-free culture supernatant fractions.

Total proteins from each fraction were precipitated with 10% tri-chloro acetic acid. Dried proteins were resuspended in SDS-PAGE sample buffer and electrophoresed in a 15% SDS-PAGE gel. Proteins were transferred to an Immobilon membrane (Millipore, Bedford, Mass.) and immunoblotted with pooled mouse serum used at a 1:20,000 dilution. Mouse serum was obtained by bleeding mice subsequent to immunization with HT-YscF. Immunoblots were blocked in 5% non-fat skim milk in 1× Tris-buffered saline plus 0.05% Tween-20 (BS). Pooled serum was added to 1% non-fat dry skim milk in 1% TTBS and incubated overnight. Detection of bound antibody was accomplished by incubation with an alkaline phosphatase conjugated goat-anti-mouse antibody. Antibody complexes were visualized by adding NBTBCIP.

Figure 5:
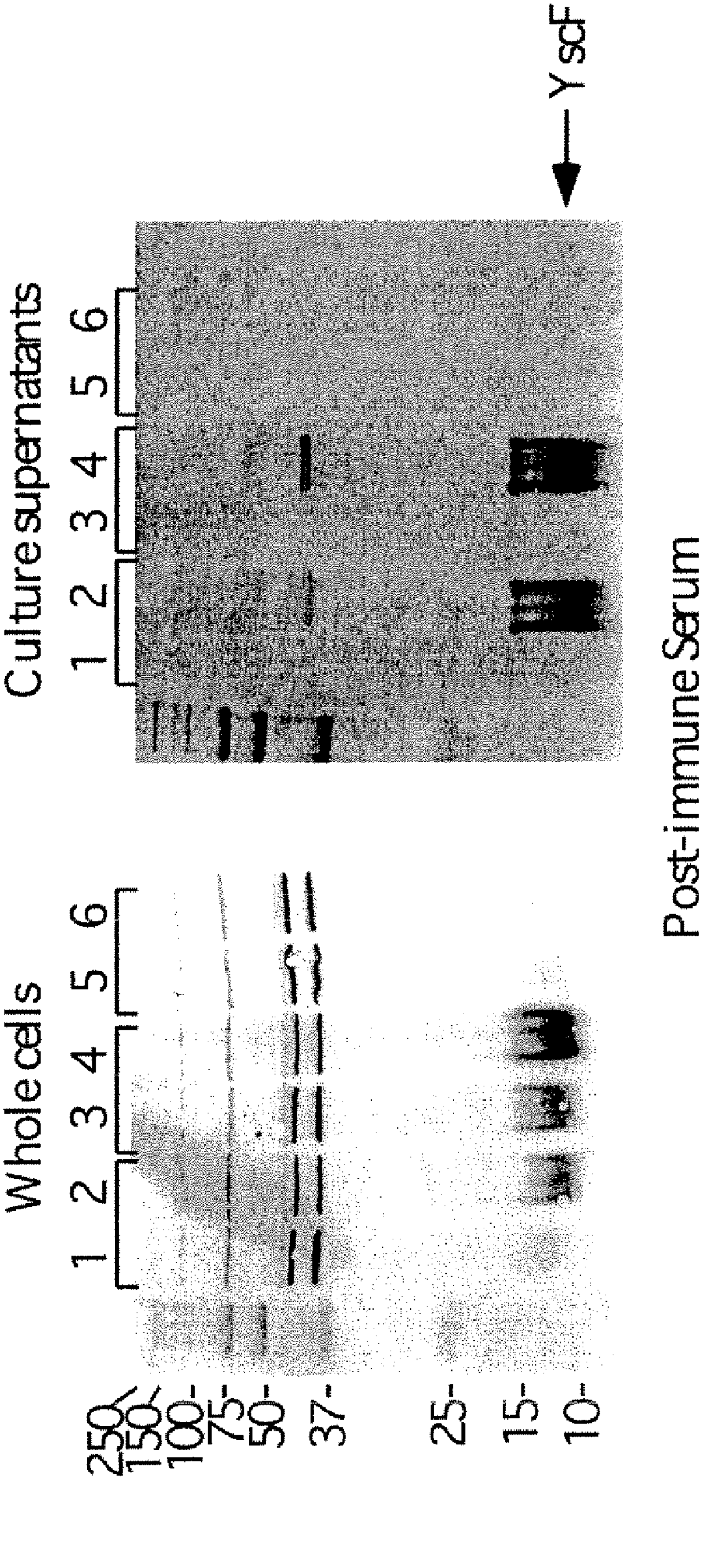
FIG. 5 represents the presence or absence of YscF protein in the culture supernatants of various *Y. pestis* strains.

Serum from several mice was pooled to control for animal-specific variation. The position and sizes for the molecular weight markers are indicated and the position of YscF is shown (FIG. 5). As seen in FIG. 5, YscF is visualized on the immunoblot as a highly reactive band of the correct size predicted for YscF and the band is only seen in strains containing the yscF gene. Importantly, no band is seen in lanes 5 and 6 that contain proteins derived from the yscF deletion strain. In lanes 1 and 2, calcium regulation of the YscF band is seen as expected. The higher molecular weight bands seen in the whole cell fraction represent cross-reactive *Y. pestis* bands that are present in samples probed with pre-immune serum (not shown). The higher molecular weight band seen in the culture supernatant fractions is consistent with the expected size of an YscF trimer.

EXAMPLE X

In another exemplary embodiment, antibodies or derivatives thereof (e.g., fragments such as Fab, $F(ab')_2$ or Fv fragments), which are directed against isolated or recombinant YscF or homologs thereof are used in passive immunotherapy, diagnostic immunoassays and in the generation of anti-idiotypic antibodies. Serum including polyclonal antibodies of derivatives thereof directed against the isolated or recombinant YscF or homologs thereof is obtained as described herein. Monospecific antibodies directed against the isolated or recombinant YscF or homologs thereof are affinity purified from polyspecific antisera by a modification of the method of Hall et al. (see, *Nature,* 311, 379-387 (1984)).

An epitope of the isolated or recombinant YscF or homologs thereof to which the antibodies bind is determined using known techniques including, but not limited to, Pepscan or microarray technology. When the amino acid residues of the epitope are determined, one skilled in the art generates peptides having amino acid residues of the epitope by artificially synthesizing the peptides of the epitope or using recombinant nucleic acid technology. The synthetic peptides are used to form a composition, vaccine or medicament to treat a disease associated with a pathogen of *Yersinia* origin or generate antibodies.

Monoclonal antibodies reactive against the isolated or recombinant YscF or homologs thereof are prepared by immunizing mice using techniques known in the art (see, Kohler and Milstein, *Nature,* 256, 495-497 (1975)). Hybridoma cells are selected by growth in hypoxanthine, thymidine and aminopterin in an appropriate cell culture medium such as Dulbecco's modified Eagle's medium. Antibody-producing hybridomas are cloned, such as by using the soft agar technique of MacPherson (see, *Soft Agar Techniques, Tissue Culture Methods and Applications*, Kruse and Paterson, eds., Academic Press, 276 (1973)). Discrete colonies are transferred into individual wells of culture plates for cultivation in an appropriate culture medium. Antibody-producing cells are identified by screening with the appropriate immunogen. Immunogen-positive hybridoma cells are maintained by techniques known in the art and specific anti-monoclonal antibodies are produced by cultivating the hydridomas in vitro or preparing ascites fluid in mice following hydridoma injection using procedures known in the art.

Anti-idiotypic antibodies are immunoglobulins which carry an "internal image" of the isolated or recombinant YscF or homologs thereof of the pathogen against which protection is desired and are used as an immunogen in a vaccine as described in Dreesman et al. (see, *J. Infect. Disease,* 151, 741 (1985)). Techniques for raising anti-idiotypic antibodies are known in the art (see, MacNamara et al., *Science* 226, 1325 (1984)).

EXAMPLE XI

A diagnostic kit including antibodies generated against isolated or recombinant YscF or homologs thereof for diagnosing disease is also included. The kit contains at least one antibody or fragment thereof directed against the isolated or recombinant YscF or homologs thereof. The immunochemical reaction employed using the kit is a sandwich reaction, an agglutination reaction, a competition reaction or an inhibition reaction, all of which are known by those of ordinary skill in the art. When the kit is used to perform a sandwich reaction, the kit includes isolated or recombinant YscF or homologs thereof bonded to a solid support, such as the inner wall of a tube or well of a plate. The kit is used to detect the presence of isolated or recombinant YscF of *Yersinia* origin or homologs thereof in fleas, mice, rats, prairie dogs, pigs, humans, cats, dogs and tissues thereof to ascertain if populations of the animals have been infected with pathogens of *Yersinia* origin.

The exemplary embodiments described herein are not meant to limit the scope of the present invention. The present invention may be carried out using embodiments different from those specifically exemplified herein. Therefore, the scope of the present invention is not limited by the exemplary embodiments, but is defined by the appended claims.

REFERENCES

1. Allaoui A., R. Schulte, and G. R. Cornelis (1995). Mutational analysis of the *Yersinia enterocolitica* virC operon: characterization of yscE, F, G, I, J, K required for Yop secretion and yscH encoding YopR. *Mol. Microbiol.* 18:343-55.
2. Blocker A., N. Jouihri, E. Larquet, P. Gounon, F. Ebel, C. Parsot, P. Sansonetti, and A. Allaoui (2001). Structure and composition of the *Shigella flexneri* "needle complex," a part of its type III secreton. *Mol. Microbiol.* 39:652-63.
3. Coligan J. E., B. M. Dunn, D. W. Speicher, and P. T. Wingfield (ed.) (1998). *Current protocols in protein science*. John Wiley & Sons, New York.
4. Cornelis G. R. (2002). The *Yersinia* Ysc-Yop "type III" weaponry. *Nat. Rev. Mol. Cell Biol.* 3:742-52.
5. Daniell S. J., N. Takahashi, R. Wilson, D. Friedberg, L. Rosenshine, F. P. Booy, R. K. Shaw, S. Knutton, G. Frankel, and S. Aizawa (2001). The filamentous type III secretion translocon of enteropathogenic *Escherichia coli. Cell Microbiol.* 3:865-71.
6. Davis K. J., D. L. Fritz, M. L. Pitt, S. L. Welkos, P. L. Worsham, and A. M. Friedlander (1996). Pathology of experimental pneumonic plague produced by fraction 1-positive and fraction 1-negative *Yersinia pestis* in African green monkeys (*Cercopithecus aethiops*). *Arch. Pathol. Lab. Med.* 120:156-63.
7. Drozdov I. G., A. P. Anisimov, S. V. Samoilova, I. N. Yezhov, S. A. Yeremin, A. V. Karlyshev, V. M. Krasilnikova, and V. I. Kravchenko (1995). Virulent non-capsulate *Yersinia pestis* variants constructed by insertion mutagenesis. *J. Med. Microbiol.* 42:264-8.
8. Du Y., E. Galyov, and A. Forsberg (1995). Genetic analysis of virulence determinants unique to *Yersinia pestis. Contrib. Microbiol. Immunol.* 13:321-4.
9. Fields K. A., M. L. Nilles, C. Cowan, and S. C. Straley (1999). Virulence role of V antigen of *Yersinia pestis* at the bacterial surface. *Infection and Immunity* 67:5395-408.

10. Haddix P. L. and S. C. Straley (1992). Structure and regulation of the *Yersinia pestis* yscBCDEF operon. *J. Bacterial.* 174:4820-8.

11. Håkansson S., K. Schesser, C. Persson, E. E. Galyov, R. Rosqvist, F. Homblé, and H. Wolf-Watz (1996). The YopB protein of *Yersinia pseudotuberculosis* is essential for the translocation of Yop effector proteins across the target cell plasma membrane and displays a contact-dependent membrane disrupting activity. *EMBO Journal* 15:5812-5823.

12. Hoiczyk E. and G. Blobel (2001). Polymerization of a single protein of the pathogen *Yersinia enterocolitica* into needles punctures eukaryotic cells. *Proc. Natl. Acad. Sci. U.S.A.* 98:4669-74.

13. Holmström A., J. Olsson, P. Cherepanov, E. Maier, R. Nordfelth, J. Pettersson, R. Benz, H. Wolf-Watz, and A. A. Forsberg (2001). LcrV is a channel size-determining component of the Yop effector translocon of *Yersinia. Mol. Microbiol.* 39:620-632.

14. Inglesby T. V., D. T. Dennis, D. A. Henderson, J. G. Bartlett, M. S. Ascher, E. Eitzen, A. D. Fine, A. M. Friedlander, J. Hauer, J. F. Koerner, M. Layton, J. McDade, M. T. Osterholm, T. O'Toole, G. Parker, T. M. Perl, P. K. Russell, M. Schoch-Spana, and K. Tonat (2000). Plague as a biological weapon: medical and public health management. *Working Group on Civilian Biodefense. Jama.* 283:2281-90.

15. Kubori T., Y. Matsushima, D. Nakamura, J. Uralil, M. Lara-Tejero, A. Sukhan, J. E. Galan, and S.-I. Aizawa (1998). Supramolecular structure of the *Salmonella typhimurium* type III protein secretion system. *Science* 280:602-605.

16. Kubori T., A. Sukhan, S. I. Aizawa, and J. E. Galan (2000). Molecular characterization and assembly of the needle complex of the *Salmonella typhimurium* type III protein secretion system. *Proc. Natl. Acad. Sci. U.S.A.* 97:10225-30.

17. Nilles M. L., K. A. Fields, and S. C. Straley (1998). The V antigen of *Yersinia pestis* regulates Yop vectorial targeting as well as Yop secretion through effects on YopB and LcrG. *Journal of Bacteriology* 180:3410-3420.

18. Nordfelth R. and R. Wolf-Watz (2001). YopB of *Yersinia enterocolitica* is essential for YopE translocation. *Infect. Immun.* 69:3516-8.

19. Perry R. D. and J. D. Fetherson (1997). *Yersinia pestis*—etiologic agent of plague. Clinical *Microbiology Reviews* 10:35-66.

20. Perry R. D., S. C. Straley, J. D. Fetherston, D. J. Rose, J. Gregor, and F. R. Blattner (1998). DNA sequencing and analysis of the low-$Ca^{2+}$-response plasmid pCD1 of *Yersinia pestis* KIM5. *Infection and Immunity* 66:4611-4623.

21. Pettersson J., A. Holmström, J. Hill, S. Leary, E. Frithz-Lindsten, A. von Euler-Matell, E. Carlsson, R. Titball, Å. Forsberg, and H. Wolf-Watz (1999). The V-antigen of *Yersinia* is surface-exposed before target cell contact and involved in virulence protein translocation. *Molecular Microbiology* 32:961-976.

22. Sekiya K., M. Ohishi, T. Ogino, K. Tamano, C, Sasakawa, and A. Abe (2001). Supermolecular structure of the enteropathogenic *Escherichia coli* type III secretion system and its direct interaction with the EspA-sheath-like structure. *Proc. Natl. Acad. Sci. U.S.A.* 98:11638-43.

23. Sory M.-P. and G. R. Cornelis (1994). Translocation of a hybrid YopE-adenylate cyclase from *Yersinia enterocolitica* into HeLa cells. *Molecular Microbiology* 14:583-594.

24. Tardy F., F. Homblé, C. Neyt, R. Wattiez, G. R. Cornelis, J.-M. Ruysschaert, and V. Cabiaux (1999). *Yersinia enterocolitica* type III secretion-translocation system: channel formation by secreted Yops. *EMBO Journal* 18:6793-6799.

25. Titball R. W. and E. D. Williamson (2001). Vaccination against bubonic and pneumonic plague. *Vaccine* 19:4175-84.

26. Welkos S. and A. O'Brien (1994). Determination of median lethal and infectious doses in animal model systems. *Methods Enzymol.* 235:29-39.

27. Welkos, S. L., K. M. Davis, L. M. Pitt, P. L. Worsham, and A. M. Freidlander (1995). Studies on the contribution of the F1 capsule-associated plasmid pFra to the virulence of *Yersinia pestis. Contrib. Microbiol. Immunol.* 13:299-305.

28. Williamson, E. D., P. M. Vesey, K. J. Gillhespy, S. M. Eley, M. Green, and R. W. Titball (1999). An IgG1 titre to the F1 and V antigens correlates with protection against plague in the mouse model. *Clin. Exp. Immunol.* 116:107-14.

29. Wilson R. K., R. K. Shaw, S. Daniell, S. Knutton, and G. Frankel (2001). Role of EscF, a putative needle complex protein, in the type III protein translocation system of enteropathogenic *Escherichia coli. Cell Microbiol.* 3:753-62.

What is claimed is:

1. An immunogenic composition comprising:

a means for providing protection to an animal against a pathogen of *Yersinia* origin, the means for providing protection comprising an isolated or recombinant YscF protein comprising SEQ ID NO: 19; and a pharmaceutically suitable excipient, wherein the protection may be assayed in a mouse challenge model.

2. The immunogenic composition of claim 1, further comprising LcrV, the F1 antigen, YopD, an attenuated *Yersinia* bacterium, a recombinant carrier bacterium including a nucleic acid encoding a YscF protein, an inactive or killed *Yersinia* bacterium or combinations thereof.

3. The immunogenic composition of claim 1, further comprising an adjuvant.

4. The immunogenic composition of claim 1, further comprising PrgI, MxiH, EscF or combinations thereof.

5. The immunogenic composition of claim 1, wherein the pathogen is *Yersinia pestis*.

6. The immunogenic composition of claim 1, wherein the means for providing protection to an animal against a pathogen of *Yersinia* origin is a His-tagged YscF protein.

7. An immunogenic composition for providing protection to an animal against a pathogen of *Yersinia* origin comprising:

a recombinant YscF protein comprising SEQ ID NO: 19; and a pharmaceutically suitable excipient, wherein the protection may be assayed in a mouse challenge model.

8. The immunogenic composition of claim 7, further comprising LcrV, the F1 antigen, YopD, an attenuated *Yersinia* bacterium, a recombinant carrier bacterium including a nucleic acid encoding a YscF protein, an inactive or killed *Yersinia* bacterium or combinations thereof.

9. The immunogenic composition of claim 7, further comprising an adjuvant.

10. The immunogenic composition of claim 7, further comprising PrgI, MxiH, EscF or mixtures thereof.

11. The immunogenic composition of claim 7, wherein the recombinant YscF comprises His-tagged YscF.

12. A composition produced by a process, the process comprising:

providing a host cell with an expression vector comprising a nucleotide sequence encoding a YscF protein capable of providing protection to an animal against a pathogen of *Yersinia* origin, the nucleotide sequence encoding a YscF protein comprising SEQ ID NO: 19;

expressing the nucleotide sequence in the host cell to produce the YscF protein;

collecting the YscF protein; and mixing the collected YscF protein with a suitable excipient.

13. The composition produced by the process of claim 12, further comprising mixing LcrV, the Fl antigen, YopD or combinations thereof with the suitable excipient.

14. The composition produced by the process of claim 12, further comprising mixing an adjuvant with the suitable excipient.

15. The composition produced by the process of claim 12, further comprising mixing PrgI, MxiH, EscF or combinations thereof with the suitable excipient.

16. A composition comprising: an isolated or recombinant YscF protein capable of providing protection to an animal against a pathogen of *Yersinia* origin, the isolated or recombinant YscF protein comprising SEQ ID NO: 19, wherein the protection may be assayed in a mouse challenge model; and a pharmaceutically acceptable excipient.

17. The immunogenic composition of claim 1, wherein the pathogen is selected from the group consisting of *Y. pestis, Y. pseudotuberculosis*, and *Y. enterocolitica*.

18. A kit for detecting an antibody capable of binding a YscF protein, the kit comprising:

an isolated or recombinant YscF protein comprising SEQ ID NO: 19;

means for detecting binding between the isolated or recombinant YscF protein and the antibody capable of binding the YscF protein; and a suitable liquid vehicle.

* * * * *

SEQUENCE LISTING

```
<160> NUMBER OF SEQ ID NOS: 20

<210> SEQ ID NO 1
<211> LENGTH: 87
<212> TYPE: PRT
<213> ORGANISM: Yersinia pestis
<220> FEATURE:
<223> OTHER INFORMATION: amino acid sequence of YscF
<220> FEATURE:
<223> OTHER INFORMATION: sequence can be found at MedLine accession
      number NP_857921.1

<400> SEQUENCE: 1

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30
```

-continued

```
Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85


<210> SEQ ID NO 2
<211> LENGTH: 264
<212> TYPE: DNA
<213> ORGANISM: Yersinia pestis
<220> FEATURE:
<223> OTHER INFORMATION: nucliec acids encoding YscF
<220> FEATURE:
<223> OTHER INFORMATION: sequence can be found at MedLine accession
      number NL_004839

<400> SEQUENCE: 2

atgagtaact tctctggatt tacgaaagga accgatatcg cagacttaga tgcggtggct      60

caaacgctca agaagccagc agacgatgca aacaaagcgg ttaatgactc gatagcagca     120

ttgaaagata agcctgacaa cccggcgcta cttgctgact tacaacattc aattaataaa     180

tggtcggtaa tttacaatat aaactcaacc atagttcgta gcatgaaaga cttaatgcaa     240

ggcatcctac agaagttccc ataa                                            264


<210> SEQ ID NO 3
<211> LENGTH: 264
<212> TYPE: DNA
<213> ORGANISM: Yersinia enterocolitica
<220> FEATURE:
<223> OTHER INFORMATION: nucleic acid encoding YscF from Y.
      enterocolitica
<220> FEATURE:
<223> OTHER INFORMATION: sequence can be found at MedLine accession
      number NC_005017

<400> SEQUENCE: 3

atgagtaatt tctctgggtt tgcaaaagga accgatatca cagacttaga tgcggtggct      60

caaacgctca agaagccagc agacggcgca aacaaagcgg ttaatgactc gatagcagcg     120

ttgaaagaga cgcctgacaa cccggcgcta cttgctgact tacaacattc aattaataaa     180

tggtcggtaa tttacaatat aagctcaacc atagttcgta gcatgaaaga cttaatgcaa     240

ggcatcctac agaagttccc ataa                                            264


<210> SEQ ID NO 4
<211> LENGTH: 87
<212> TYPE: PRT
<213> ORGANISM: Yersinia enterocolitica
<220> FEATURE:
<223> OTHER INFORMATION: amino acid sequence of YscF from Y.
      enterocolitica
<220> FEATURE:
<223> OTHER INFORMATION: sequence can be found at MedLine accession
      number NP_863538.1

<400> SEQUENCE: 4

Met Ser Asn Phe Ser Gly Phe Ala Lys Gly Thr Asp Ile Thr Asp Leu
1               5                   10                  15

Asp Ala Val Ala Gln Thr Leu Lys Lys Pro Ala Asp Asp Ala Asn Lys
            20                  25                  30
```

-continued

```
Ala Val Asn Asp Ser Ile Ala Ala Leu Lys Asp Thr Pro Asp Asn Pro
        35                  40                  45

Ala Leu Leu Ala Asp Leu Gln His Ser Ile Asn Lys Trp Ser Val Ile
    50                  55                  60

Tyr Asn Met Ser Ser Thr Ile Val Arg Ser Met Lys Asp Leu Met Gln
65                  70                  75                  80

Gly Ile Leu Gln Lys Phe Pro
                85


<210> SEQ ID NO 5
<211> LENGTH: 80
<212> TYPE: PRT
<213> ORGANISM: Salmonella enterica
<220> FEATURE:
<223> OTHER INFORMATION: amino acid sequence of PrgI
<220> FEATURE:
<223> OTHER INFORMATION: sequence can be found at MedLine accession
      number CAD05980.1

<400> SEQUENCE: 5

Met Pro Thr Ser Trp Ser Gly Tyr Leu Asp Glu Val Ser Ala Lys Phe
1               5                   10                  15

Asp Lys Gly Val Asp Asn Leu Gln Thr Gln Val Thr Glu Ala Leu Asp
            20                  25                  30

Lys Leu Ala Ala Lys Pro Ser Asp Pro Ala Leu Leu Ala Ala Tyr Gln
        35                  40                  45

Ser Lys Leu Ser Glu Tyr Asn Leu Tyr Arg Asn Ala Gln Ser Asn Thr
    50                  55                  60

Val Lys Val Phe Lys Asp Ile Asp Ala Ala Ile Ile Gln Asn Phe Arg
65                  70                  75                  80


<210> SEQ ID NO 6
<211> LENGTH: 243
<212> TYPE: DNA
<213> ORGANISM: Salmonella enterica
<220> FEATURE:
<223> OTHER INFORMATION: sequence can be found at MedLine accession
      number AL627276
<220> FEATURE:
<223> OTHER INFORMATION: nucleic acid encoding PrgI

<400> SEQUENCE: 6

atgccaacat cttggtcagg ctatctggat gaagtttcag caaaatttga taagggcgtt      60

gataatctac aaacgcaggt aacagaggcg ctggataaat tagcagcaaa accctccgat     120

ccggcgctac tggcggcgta tcagagtaag ctctcggaat ataacttgta ccgtaacgcg     180

caatcgaaca cggtaaaagt ctttaaggat attgatgctg ccattattca gaacttccgt     240

taa                                                                   243


<210> SEQ ID NO 7
<211> LENGTH: 83
<212> TYPE: PRT
<213> ORGANISM: Shigella flexneri
<220> FEATURE:
<223> OTHER INFORMATION: amino acid sequence of MxiH
<220> FEATURE:
<223> OTHER INFORMATION: sequence can be found at MedLine accession
      number NP_858270.1

<400> SEQUENCE: 7

Met Ser Val Thr Val Pro Asn Asp Asp Trp Thr Leu Ser Ser Leu Ser
1               5                   10                  15
```

-continued

```
Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg


<210> SEQ ID NO 8
<211> LENGTH: 252
<212> TYPE: DNA
<213> ORGANISM: Shigella flexneri
<220> FEATURE:
<223> OTHER INFORMATION: nucleic acid encoding MxiH
<220> FEATURE:
<223> OTHER INFORMATION: sequence can be found at MedLine accession
      number Nc_004851

<400> SEQUENCE: 8

atgagtgtta cagtaccgaa tgatgattgg acattgagtt cattatctga aacttttgat      60

gatggaactc aaacattaca aggtgaacta acattggcac tagataaatt agctaaaaat     120

ccttcgaatc cacagttgct ggctgaatac caaagtaaat tatctgaata tacattatat     180

aggaacgcgc aatccaatac agtgaaagtg attaaggatg ttgatgctgc aattattcaa     240

aacttcagat aa                                                         252


<210> SEQ ID NO 9
<211> LENGTH: 73
<212> TYPE: PRT
<213> ORGANISM: Escherichia coli
<220> FEATURE:
<223> OTHER INFORMATION: amino acid sequence of EscF
<220> FEATURE:
<223> OTHER INFORMATION: sequence can be found at MedLine accession
      number NP_312579.1

<400> SEQUENCE: 9

Met Asn Leu Ser Glu Ile Thr Gln Gln Met Gly Glu Val Gly Lys Thr
1               5                   10                  15

Leu Ser Asp Ser Val Pro Glu Leu Leu Asn Ser Thr Asp Leu Val Asn
            20                  25                  30

Asp Pro Glu Lys Met Leu Glu Leu Gln Phe Ala Val Gln Gln Tyr Ser
        35                  40                  45

Ala Tyr Val Asn Val Glu Ser Gly Met Leu Lys Thr Ile Lys Asp Leu
    50                  55                  60

Val Ser Thr Ile Ser Asn Arg Ser Phe
65                  70


<210> SEQ ID NO 10
<211> LENGTH: 222
<212> TYPE: DNA
<213> ORGANISM: Escherichia coli
<220> FEATURE:
<223> OTHER INFORMATION: nucleic acid encoding EscF
<220> FEATURE:
<223> OTHER INFORMATION: sequence can be found at MedLine accession
      number NC_002695

<400> SEQUENCE: 10
```

-continued

```
atgaatttat ctgaaattac tcaacaaatg ggtgaagtag gtaaaacgct gagcgattct      60

gtgccagagt tacttaatag caccgatttg gttaatgacc ctgaaaaaat gttagagttg     120

cagtttgcgg ttcagcaata ttctgcttat gttaacgtag aaagtggaat gttgaaaacg     180

ataaaagatc tggtctcaac catttctaac cgtagttttt aa                        222
```

<210> SEQ ID NO 11
<211> LENGTH: 240
<212> TYPE: DNA
<213> ORGANISM: Yersinia pestis
<220> FEATURE:
<223> OTHER INFORMATION: nucleic acid encoding HT-YscF; an example of a recombinant YscF
<220> FEATURE:
<221> NAME/KEY: misc_feature
<222> LOCATION: (214)..(237)
<223> OTHER INFORMATION: His-tag sequence

<400> SEQUENCE: 11

```
atgagtaact tctctggatt tacgaaagga accgatgatg caaacaaagc ggttaatgac      60

tcgatagcag cattgaaaga taagcctgac aacccggcgc tacttgctga cttacaacat     120

tcaattaata aatggtcggt aatttacaat ataaactcaa ccatagttcg tagcatgaaa     180

gacttaatgc aaggcatcct acagaagttc ccactcgagc accaccacca ccaccactga     240
```

<210> SEQ ID NO 12
<211> LENGTH: 95
<212> TYPE: PRT
<213> ORGANISM: Yersinia pestis
<220> FEATURE:
<223> OTHER INFORMATION: amino acid sequence of HT-YscF; an example of a recombinant YscF
<220> FEATURE:
<221> NAME/KEY: misc_feature
<222> LOCATION: (88)..(95)
<223> OTHER INFORMATION: His-tag

<400> SEQUENCE: 12

```
Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro Leu Glu His His His His His His
                85                  90                  95
```

<210> SEQ ID NO 13
<211> LENGTH: 5537
<212> TYPE: DNA
<213> ORGANISM: Artificial Sequence
<220> FEATURE:
<223> OTHER INFORMATION: pMJ119
<220> FEATURE:
<221> NAME/KEY: misc_feature
<222> LOCATION: (563)..(1375)
<223> OTHER INFORMATION: kan encoded on complementary strand
<220> FEATURE:
<221> NAME/KEY: misc_feature
<222> LOCATION: (3518)..(4597)
<223> OTHER INFORMATION: LacI encoded on complementary strand -continued
<220> FEATURE:
<221> NAME/KEY: promoter
<222> LOCATION: (4983)..(5000)
<223> OTHER INFORMATION: T7 promoter
<220> FEATURE:
<221> NAME/KEY: misc_feature
<222> LOCATION: (5001)..(5001)
<223> OTHER INFORMATION: T7 transcription start
<220> FEATURE:
<221> NAME/KEY: misc_feature
<222> LOCATION: (5072)..(5104)
<223> OTHER INFORMATION: T7 Tag
<220> FEATURE:
<221> NAME/KEY: CDS
<222> LOCATION: (5114)..(5401)
<223> OTHER INFORMATION: HT-YscF
<220> FEATURE:
<221> NAME/KEY: misc_feature
<222> LOCATION: (5381)..(5398)
<223> OTHER INFORMATION: His-tag sequence
<220> FEATURE:
<221> NAME/KEY: terminator
<222> LOCATION: (5466)..(5512)
<223> OTHER INFORMATION: T7 terminator

<400> SEQUENCE: 13
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560

-continued

```
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggg taatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
```

-continued

```
tcggctgaat ttgattgcga gtgagatatt tatgccagcc agccagacgc agacgcgccg   4020

agacagaact taatgggccc gctaacagcg cgatttgctg gtgacccaat gcgaccagat   4080

gctccacgcc cagtcgcgta ccgtcttcat gggagaaaat aatactgttg atgggtgtct   4140

ggtcagagac atcaagaaat aacgccggaa cattagtgca ggcagcttcc acagcaatgg   4200

catcctggtc atccagcgga tagttaatga tcagcccact gacgcgttgc gcgagaagat   4260

tgtgcaccgc cgctttacag gcttcgacgc cgcttcgttc taccatcgac accaccacgc   4320

tggcacccag ttgatcggcg cgagatttaa tcgccgcgac aatttgcgac ggcgcgtgca   4380

gggccagact ggaggtggca acgccaatca gcaacgactg tttgcccgcc agttgttgtg   4440

ccacgcggtt gggaatgtaa ttcagctccg ccatcgccgc ttccactttt tcccgcgttt   4500

tcgcagaaac gtggctggcc tggttcacca cgcgggaaac ggtctgataa gagacaccgg   4560

catactctgc gacatcgtat aacgttactg gtttcacatt caccaccctg aattgactct   4620

cttccgggcg ctatcatgcc ataccgcgaa aggttttgcg ccattcgatg gtgtccggga   4680

tctcgacgct ctcccttatg cgactcctgc attaggaagc agcccagtag taggttgagg   4740

ccgttgagca ccgccgccgc aaggaatggt gcatgcaagg agatggcgcc caacagtccc   4800

ccggccacgg ggcctgccac catacccacg ccgaaacaag cgctcatgag cccgaagtgg   4860

cgagcccgat cttccccatc ggtgatgtcg gcgatatagg cgccagcaac cgcacctgtg   4920

gcgccggtga tgccggccac gatgcgtccg gcgtagagga tcgagatctc gatcccgcga   4980

aattaatacg actcactata ggggaattgt gagcggataa caattcccct ctagaaataa   5040

ttttgtttaa ctttaagaag gagatataca tatggctagc atgactggtg gacagcaaat   5100

gggtcgggat ccg atg agt aac ttc tct gga ttt acg aaa gga acc gat      5149
               Met Ser Asn Phe Ser Gly Phe Thr Lys Gly Thr Asp
               1               5                   10

atc gca gac tta gat gcg gtg gct caa acg ctc aag aag cca gca gac      5197
Ile Ala Asp Leu Asp Ala Val Ala Gln Thr Leu Lys Lys Pro Ala Asp
        15                  20                  25

gat gca aac aaa gcg gtt aat gac tcg ata gca gca ttg aaa gat aag      5245
Asp Ala Asn Lys Ala Val Asn Asp Ser Ile Ala Ala Leu Lys Asp Lys
    30                  35                  40

cct gac aac ccg gcg cta ctt gct gac tta caa cat tca att aat aaa      5293
Pro Asp Asn Pro Ala Leu Leu Ala Asp Leu Gln His Ser Ile Asn Lys
45                  50                  55                  60

tgg tcg gta att tac aat ata aac tca acc ata gtt cgt agc atg aaa      5341
Trp Ser Val Ile Tyr Asn Ile Asn Ser Thr Ile Val Arg Ser Met Lys
                65                  70                  75

gac tta atg caa ggc atc cta cag aag ttc cca ctc gag cac cac cac      5389
Asp Leu Met Gln Gly Ile Leu Gln Lys Phe Pro Leu Glu His His His
            80                  85                  90

cac cac cac tga gatccggctg ctaacaaagc ccgaaaggaa gctgagttgg         5441
His His His
        95

ctgctgccac cgctgagcaa taactagcat aaccccttgg ggcctctaaa cgggtcttga   5501

ggggtttttt gctgaaagga ggaactatat ccggat                             5537
```

```
<210> SEQ ID NO 14
<211> LENGTH: 5309
<212> TYPE: DNA
<213> ORGANISM: Artificial Sequence
<220> FEATURE:
<223> OTHER INFORMATION: pET24b
<220> FEATURE:
```

-continued

<221> NAME/KEY: terminator
<222> LOCATION: (26)..(72)
<223> OTHER INFORMATION: T7 terminator
<220> FEATURE:
<221> NAME/KEY: misc_feature
<222> LOCATION: (140)..(157)
<223> OTHER INFORMATION: His-tag sequence
<220> FEATURE:
<221> NAME/KEY: misc_feature
<222> LOCATION: (206)..(238)
<223> OTHER INFORMATION: T7 Tag
<220> FEATURE:
<221> NAME/KEY: misc_feature
<222> LOCATION: (309)..(309)
<220> FEATURE:
<221> NAME/KEY: misc_feature
<222> LOCATION: (309)..(309)
<223> OTHER INFORMATION: T7 transcription start
<220> FEATURE:
<221> NAME/KEY: promoter
<222> LOCATION: (310)..(327)
<223> OTHER INFORMATION: T7 promoter
<220> FEATURE:
<221> NAME/KEY: misc_feature
<222> LOCATION: (713)..(716)
<223> OTHER INFORMATION: Alternate start codon "gtg"
<220> FEATURE:
<221> NAME/KEY: CDS
<222> LOCATION: (713)..(1792)
<223> OTHER INFORMATION: lacI
<220> FEATURE:
<221> NAME/KEY: CDS
<222> LOCATION: (3935)..(4747)
<223> OTHER INFORMATION: kan

<400> SEQUENCE: 14

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagtgcggcc gcaagcttgt    180

cgacggagct cgaattcgga tcccgaccca tttgctgtcc accagtcatg ctagccatat    240

gtatatctcc ttcttaaagt taaacaaaat tatttctaga ggggaattgt tatccgctca    300

caattcccct atagtgagtc gtattaattt cgcgggatcg agatctcgat cctctacgcc    360

ggacgcatcg tggccggcat caccggcgcc acaggtgcgg ttgctggcgc ctatatcgcc    420

gacatcaccg atggggaaga tcgggctcgc cacttcgggc tcatgagcgc ttgtttcggc    480

gtgggtatgg tggcaggccc cgtggccggg ggactgttgg gcgccatctc cttgcatgca    540

ccattccttg cggcggcggt gctcaacggc ctcaacctac tactgggctg cttcctaatg    600

caggagtcgc ataagggaga gcgtcgagat cccggacacc atcgaatggc gcaaaacctt    660

tcgcggtatg gcatgatagc gcccggaaga gagtcaattc agggtggtga at gtg aaa    718
                                                          Met Lys
                                                          1

cca gta acg tta tac gat gtc gca gag tat gcc ggt gtc tct tat cag      766
Pro Val Thr Leu Tyr Asp Val Ala Glu Tyr Ala Gly Val Ser Tyr Gln
        5                   10                  15

acc gtt tcc cgc gtg gtg aac cag gcc agc cac gtt tct gcg aaa acg      814
Thr Val Ser Arg Val Val Asn Gln Ala Ser His Val Ser Ala Lys Thr
    20                  25                  30

cgg gaa aaa gtg gaa gcg gcg atg gcg gag ctg aat tac att ccc aac      862
Arg Glu Lys Val Glu Ala Ala Met Ala Glu Leu Asn Tyr Ile Pro Asn
35                  40                  45                  50

cgc gtg gca caa caa ctg gcg ggc aaa cag tcg ttg ctg att ggc gtt      910
Arg Val Ala Gln Gln Leu Ala Gly Lys Gln Ser Leu Leu Ile Gly Val
                55                  60                  65
```

-continued

```
gcc acc tcc agt ctg gcc ctg cac gcg ccg tcg caa att gtc gcg gcg      958
Ala Thr Ser Ser Leu Ala Leu His Ala Pro Ser Gln Ile Val Ala Ala
            70                  75                  80

att aaa tct cgc gcc gat caa ctg ggt gcc agc gtg gtg gtg tcg atg     1006
Ile Lys Ser Arg Ala Asp Gln Leu Gly Ala Ser Val Val Val Ser Met
        85                  90                  95

gta gaa cga agc ggc gtc gaa gcc tgt aaa gcg gcg gtg cac aat ctt     1054
Val Glu Arg Ser Gly Val Glu Ala Cys Lys Ala Ala Val His Asn Leu
    100                 105                 110

ctc gcg caa cgc gtc agt ggg ctg atc att aac tat ccg ctg gat gac     1102
Leu Ala Gln Arg Val Ser Gly Leu Ile Ile Asn Tyr Pro Leu Asp Asp
115                 120                 125                 130

cag gat gcc att gct gtg gaa gct gcc tgc act aat gtt ccg gcg tta     1150
Gln Asp Ala Ile Ala Val Glu Ala Ala Cys Thr Asn Val Pro Ala Leu
                135                 140                 145

ttt ctt gat gtc tct gac cag aca ccc atc aac agt att att ttc tcc     1198
Phe Leu Asp Val Ser Asp Gln Thr Pro Ile Asn Ser Ile Ile Phe Ser
            150                 155                 160

cat gaa gac ggt acg cga ctg ggc gtg gag cat ctg gtc gca ttg ggt     1246
His Glu Asp Gly Thr Arg Leu Gly Val Glu His Leu Val Ala Leu Gly
        165                 170                 175

cac cag caa atc gcg ctg tta gcg ggc cca tta agt tct gtc tcg gcg     1294
His Gln Gln Ile Ala Leu Leu Ala Gly Pro Leu Ser Ser Val Ser Ala
    180                 185                 190

cgt ctg cgt ctg gct ggc tgg cat aaa tat ctc act cgc aat caa att     1342
Arg Leu Arg Leu Ala Gly Trp His Lys Tyr Leu Thr Arg Asn Gln Ile
195                 200                 205                 210

cag ccg ata gcg gaa cgg gaa ggc gac tgg agt gcc atg tcc ggt ttt     1390
Gln Pro Ile Ala Glu Arg Glu Gly Asp Trp Ser Ala Met Ser Gly Phe
                215                 220                 225

caa caa acc atg caa atg ctg aat gag ggc atc gtt ccc act gcg atg     1438
Gln Gln Thr Met Gln Met Leu Asn Glu Gly Ile Val Pro Thr Ala Met
            230                 235                 240

ctg gtt gcc aac gat cag atg gcg ctg ggc gca atg cgc gcc att acc     1486
Leu Val Ala Asn Asp Gln Met Ala Leu Gly Ala Met Arg Ala Ile Thr
        245                 250                 255

gag tcc ggg ctg cgc gtt ggt gcg gat atc tcg gta gtg gga tac gac     1534
Glu Ser Gly Leu Arg Val Gly Ala Asp Ile Ser Val Val Gly Tyr Asp
    260                 265                 270

gat acc gaa gac agc tca tgt tat atc ccg ccg tta acc acc atc aaa     1582
Asp Thr Glu Asp Ser Ser Cys Tyr Ile Pro Pro Leu Thr Thr Ile Lys
275                 280                 285                 290

cag gat ttt cgc ctg ctg ggg caa acc agc gtg gac cgc ttg ctg caa     1630
Gln Asp Phe Arg Leu Leu Gly Gln Thr Ser Val Asp Arg Leu Leu Gln
                295                 300                 305

ctc tct cag ggc cag gcg gtg aag ggc aat cag ctg ttg ccc gtc tca     1678
Leu Ser Gln Gly Gln Ala Val Lys Gly Asn Gln Leu Leu Pro Val Ser
            310                 315                 320

ctg gtg aaa aga aaa acc acc ctg gcg ccc aat acg caa acc gcc tct     1726
Leu Val Lys Arg Lys Thr Thr Leu Ala Pro Asn Thr Gln Thr Ala Ser
        325                 330                 335

ccc cgc gcg ttg gcc gat tca tta atg cag ctg gca cga cag gtt tcc     1774
Pro Arg Ala Leu Ala Asp Ser Leu Met Gln Leu Ala Arg Gln Val Ser
    340                 345                 350

cga ctg gaa agc ggg cag tgagcgcaac gcaattaatg taagttagct            1822
Arg Leu Glu Ser Gly Gln
355                 360

cactcattag gcaccgggat ctcgaccgat gcccttgaga gccttcaacc cagtcagctc   1882

cttccggtgg gcgcggggca tgactatcgt cgccgcactt atgactgtct tctttatcat   1942
```

-continued

```
gcaactcgta ggacaggtgc cggcagcgct ctgggtcatt ttcggcgagg accgctttcg   2002

ctggagcgcg acgatgatcg gcctgtcgct tgcggtattc ggaatcttgc acgccctcgc   2062

tcaagccttc gtcactggtc ccgccaccaa acgtttcggc gagaagcagg ccattatcgc   2122

cggcatggcg gccccacggg tgcgcatgat cgtgctcctg tcgttgagga cccggctagg   2182

ctggcggggt tgccttactg gttagcagaa tgaatcaccg atacgcgagc gaacgtgaag   2242

cgactgctgc tgcaaaacgt ctgcgacctg agcaacaaca tgaatggtct tcggtttccg   2302

tgtttcgtaa agtctggaaa cgcggaagtc agcgccctgc accattatgt tccggatctg   2362

catcgcagga tgctgctggc taccctgtgg aacacctaca tctgtattaa cgaagcgctg   2422

gcattgaccc tgagtgattt ttctctggtc ccgccgcatc cataccgcca gttgtttacc   2482

ctcacaacgt tccagtaacc gggcatgttc atcatcagta acccgtatcg tgagcatcct   2542

ctctcgtttc atcggtatca ttacccccat gaacagaaat cccccttaca cggaggcatc   2602

agtgaccaaa caggaaaaaa ccgcccttaa catggcccgc tttatcagaa gccagacatt   2662

aacgcttctg gagaaactca acgagctgga cgcggatgaa caggcagaca tctgtgaatc   2722

gcttcacgac cacgctgatg agctttaccg cagctgcctc gcgcgtttcg gtgatgacgg   2782

tgaaaacctc tgacacatgc agctcccgga gacggtcaca gcttgtctgt aagcggatgc   2842

cgggagcaga caagcccgtc agggcgcgtc agcgggtgtt ggcgggtgtc ggggcgcagc   2902

catgacccag tcacgtagcg atagcggagt gtatactggc ttaactatgc ggcatcagag   2962

cagattgtac tgagagtgca ccatatatgc ggtgtgaaat accgcacaga tgcgtaagga   3022

gaaaataccg catcaggcgc tcttccgctt cctcgctcac tgactcgctg cgctcggtcg   3082

ttcggctgcg gcgagcggta tcagctcact caaaggcggt aatacggtta tccacagaat   3142

caggggataa cgcaggaaag aacatgtgag caaaaggcca gcaaaaggcc aggaaccgta   3202

aaaaggccgc gttgctggcg tttttccata ggctccgccc ccctgacgag catcacaaaa   3262

atcgacgctc aagtcagagg tggcgaaacc cgacaggact ataaagatac caggcgtttc   3322

cccctggaag ctccctcgtg cgctctcctg ttccgaccct gccgcttacc ggatacctgt   3382

ccgcctttct cccttcggga agcgtggcgc tttctcatag ctcacgctgt aggtatctca   3442

gttcggtgta ggtcgttcgc tccaagctgg gctgtgtgca cgaacccccc gttcagcccg   3502

accgctgcgc cttatccggt aactatcgtc ttgagtccaa cccggtaaga cacgacttat   3562

cgccactggc agcagccact ggtaacagga ttagcagagc gaggtatgta ggcggtgcta   3622

cagagttctt gaagtggtgg cctaactacg gctacactag aaggacagta tttggtatct   3682

gcgctctgct gaagccagtt accttcggaa aaagagttgg tagctcttga tccggcaaac   3742

aaaccaccgc tggtagcggt ggtttttttg tttgcaagca gcagattacg cgcagaaaaa   3802

aaggatctca agaagatcct ttgatctttt ctacggggtc tgacgctcag tggaacgaaa   3862

actcacgtta agggattttg gtcatgaaca ataaaactgt ctgcttacat aaacagtaat   3922

acaaggggtg tt atg agc cat att caa cgg gaa acg tct tgc tct agg ccg   3973
              Met Ser His Ile Gln Arg Glu Thr Ser Cys Ser Arg Pro
                                  365                 370

cga tta aat tcc aac atg gat gct gat tta tat ggg tat aaa tgg gct     4021
Arg Leu Asn Ser Asn Met Asp Ala Asp Leu Tyr Gly Tyr Lys Trp Ala
    375                 380                 385

cgc gat aat gtc ggg caa tca ggt gcg aca atc tat cga ttg tat ggg     4069
Arg Asp Asn Val Gly Gln Ser Gly Ala Thr Ile Tyr Arg Leu Tyr Gly
390                 395                 400                 405
```

-continued

```
aag ccc gat gcg cca gag ttg ttt ctg aaa cat ggc aaa ggt agc gtt      4117
Lys Pro Asp Ala Pro Glu Leu Phe Leu Lys His Gly Lys Gly Ser Val
            410                 415                 420

gcc aat gat gtt aca gat gag atg gtc aga cta aac tgg ctg acg gaa      4165
Ala Asn Asp Val Thr Asp Glu Met Val Arg Leu Asn Trp Leu Thr Glu
            425                 430                 435

ttt atg cct ctt ccg acc atc aag cat ttt atc cgt act cct gat gat      4213
Phe Met Pro Leu Pro Thr Ile Lys His Phe Ile Arg Thr Pro Asp Asp
        440                 445                 450

gca tgg tta ctc acc act gcg atc ccc ggg aaa aca gca ttc cag gta      4261
Ala Trp Leu Leu Thr Thr Ala Ile Pro Gly Lys Thr Ala Phe Gln Val
    455                 460                 465

tta gaa gaa tat cct gat tca ggt gaa aat att gtt gat gcg ctg gca      4309
Leu Glu Glu Tyr Pro Asp Ser Gly Glu Asn Ile Val Asp Ala Leu Ala
470                 475                 480                 485

gtg ttc ctg cgc cgg ttg cat tcg att cct gtt tgt aat tgt cct ttt      4357
Val Phe Leu Arg Arg Leu His Ser Ile Pro Val Cys Asn Cys Pro Phe
            490                 495                 500

aac agc gat cgc gta ttt cgt ctc gct cag gcg caa tca cga atg aat      4405
Asn Ser Asp Arg Val Phe Arg Leu Ala Gln Ala Gln Ser Arg Met Asn
            505                 510                 515

aac ggt ttg gtt gat gcg agt gat ttt gat gac gag cgt aat ggc tgg      4453
Asn Gly Leu Val Asp Ala Ser Asp Phe Asp Asp Glu Arg Asn Gly Trp
        520                 525                 530

cct gtt gaa caa gtc tgg aaa gaa atg cat aaa ctt ttg cca ttc tca      4501
Pro Val Glu Gln Val Trp Lys Glu Met His Lys Leu Leu Pro Phe Ser
    535                 540                 545

ccg gat tca gtc gtc act cat ggt gat ttc tca ctt gat aac ctt att      4549
Pro Asp Ser Val Val Thr His Gly Asp Phe Ser Leu Asp Asn Leu Ile
550                 555                 560                 565

ttt gac gag ggg aaa tta ata ggt tgt att gat gtt gga cga gtc gga      4597
Phe Asp Glu Gly Lys Leu Ile Gly Cys Ile Asp Val Gly Arg Val Gly
            570                 575                 580

atc gca gac cga tac cag gat ctt gcc atc cta tgg aac tgc ctc ggt      4645
Ile Ala Asp Arg Tyr Gln Asp Leu Ala Ile Leu Trp Asn Cys Leu Gly
            585                 590                 595

gag ttt tct cct tca tta cag aaa cgg ctt ttt caa aaa tat ggt att      4693
Glu Phe Ser Pro Ser Leu Gln Lys Arg Leu Phe Gln Lys Tyr Gly Ile
        600                 605                 610

gat aat cct gat atg aat aaa ttg cag ttt cat ttg atg ctc gat gag      4741
Asp Asn Pro Asp Met Asn Lys Leu Gln Phe His Leu Met Leu Asp Glu
    615                 620                 625

ttt ttc taagaattaa ttcatgagcg gatacatatt tgaatgtatt tagaaaaata      4797
Phe Phe
630

aacaaatagg ggttccgcgc acatttcccc gaaaagtgcc acctgaaatt gtaaacgtta   4857

atattttgtt aaaattcgcg ttaaattttt gttaaatcag ctcatttttt aaccaatagg   4917

ccgaaatcgg caaaatccct tataaatcaa aagaatagac cgagataggg ttgagtgttg   4977

ttccagtttg gaacaagagt ccactattaa agaacgtgga ctccaacgtc aaagggcgaa   5037

aaaccgtcta tcagggcgat ggcccactac gtgaaccatc accctaatca agttttttgg   5097

ggtcgaggtg ccgtaaagca ctaaatcgga accctaaagg gagcccccga tttagagctt   5157

gacggggaaa gccggcgaac gtggcgagaa aggaagggaa gaaagcgaaa ggagcgggcg   5217

ctagggcgct ggcaagtgta gcggtcacgc tgcgcgtaac caccacaccc gccgcgctta   5277

atgcgccgct acagggcgcg tcccattcgc ca                                 5309
```

-continued

```
<210> SEQ ID NO 15
<211> LENGTH: 30
<212> TYPE: DNA
<213> ORGANISM: Artificial Sequence
<220> FEATURE:
<223> OTHER INFORMATION: primer, HT-YscF Start

<400> SEQUENCE: 15

cgggatccga tgagtaactt ctctggattt                                    30


<210> SEQ ID NO 16
<211> LENGTH: 30
<212> TYPE: DNA
<213> ORGANISM: Artificial Sequence
<220> FEATURE:
<223> OTHER INFORMATION: primer, HT-YscF Stop

<400> SEQUENCE: 16

ccgctcgagt gggaacttct gtaggatgcc                                    30


<210> SEQ ID NO 17
<211> LENGTH: 87
<212> TYPE: PRT
<213> ORGANISM: Yersinia pestis KIM5
<220> FEATURE:
<223> OTHER INFORMATION: YscF amino acid seuquence from Y. pestis KIM5
<220> FEATURE:
<223> OTHER INFORMATION: sequence can be found at MedLine accession
      number NC_004839

<400> SEQUENCE: 17

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85


<210> SEQ ID NO 18
<211> LENGTH: 87
<212> TYPE: PRT
<213> ORGANISM: Yersinia pestis CO92
<220> FEATURE:
<223> OTHER INFORMATION: YscF amino acid sequence from Y. pestis CO92
<220> FEATURE:
<223> OTHER INFORMATION: sequence can be found at MedLine accession
      number NC_003131

<400> SEQUENCE: 18

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60
```

-continued

```
Tyr Asn Ile Asn Ser Thr Ile Val Arg Ser Met Lys Asp Leu Met Gln
65                  70                  75                  80

Gly Ile Leu Gln Lys Phe Pro
                85


<210> SEQ ID NO 19
<211> LENGTH: 87
<212> TYPE: PRT
<213> ORGANISM: Artificial Sequence
<220> FEATURE:
<223> OTHER INFORMATION: Consensus sequence for YscF

<400> SEQUENCE: 19

Met Ser Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro
                85


<210> SEQ ID NO 20
<211> LENGTH: 4884
<212> TYPE: DNA
<213> ORGANISM: Artificial Sequence
<220> FEATURE:
<223> OTHER INFORMATION: pBAD18-YscF
<220> FEATURE:
<221> NAME/KEY: misc_feature
<222> LOCATION: (96)..(974)
<223> OTHER INFORMATION: araC
<220> FEATURE:
<221> NAME/KEY: misc_feature
<222> LOCATION: (1003)..(1020)
<223> OTHER INFORMATION: operator 02
<220> FEATURE:
<221> NAME/KEY: promoter
<222> LOCATION: (1125)..(1153)
<223> OTHER INFORMATION: Pc promoter
<220> FEATURE:
<221> NAME/KEY: misc_feature
<222> LOCATION: (1161)..(1182)
<223> OTHER INFORMATION: operator 01
<220> FEATURE:
<221> NAME/KEY: misc_feature
<222> LOCATION: (1204)..(1217)
<223> OTHER INFORMATION: CAP site
<220> FEATURE:
<221> NAME/KEY: misc_feature
<222> LOCATION: (1213)..(1251)
<223> OTHER INFORMATION: operator I2 + I1
<220> FEATURE:
<221> NAME/KEY: promoter
<222> LOCATION: (1250)..(1277)
<223> OTHER INFORMATION: PBAD promoter
<220> FEATURE:
<221> NAME/KEY: CDS
<222> LOCATION: (1323)..(1586)
<223> OTHER INFORMATION: YscF
<220> FEATURE:
<221> NAME/KEY: misc_feature
<222> LOCATION: (1634)..(2059)
<223> OTHER INFORMATION: rrnB
<220> FEATURE:
<221> NAME/KEY: terminator
```

-continued

<222> LOCATION: (1634)..(2059)
<223> OTHER INFORMATION: rrnB
<220> FEATURE:
<221> NAME/KEY: promoter
<222> LOCATION: (2114)..(2120)
<223> OTHER INFORMATION: bla P3 promoter
<220> FEATURE:
<221> NAME/KEY: misc_feature
<222> LOCATION: (2152)..(3015)
<223> OTHER INFORMATION: bla
<220> FEATURE:
<221> NAME/KEY: rep_origin
<222> LOCATION: (3051)..(3509)
<223> OTHER INFORMATION: M13 origin
<220> FEATURE:
<221> NAME/KEY: rep_origin
<222> LOCATION: (3515)..(4212)
<223> OTHER INFORMATION: pBR322 origin

<400> SEQUENCE: 20
atcgatgcat aatgtgcctg tcaaatggac gaagcaggga ttctgcaaac cctatgctac 60
tccgtcaagc cgtcaattgt ctgattcgtt accaattatg acaacttgac ggctacatca 120
ttcacttttt cttcacaacc ggcacggaac tcgctcgggc tggccccggt gcattttta 180 aatacccgcg agaaatagag ttgatcgtca aaaccaacat tgcgaccgac ggtggcgata 240
ggcatccggg tggtgctcaa aagcagcttc gcctggctga tacgttggtc ctcgcgccag 300
cttaagacgc taatccctaa ctgctggcgg aaaagatgtg acagacgcga cggcgacaag 360
caaacatgct gtgcgacgct ggcgatatca aaattgctgt ctgccaggtg atcgctgatg 420
tactgacaag cctcgcgtac ccgattatcc atcggtggat ggagcgactc gttaatcgct 480
tccatgcgcc gcagtaacaa ttgctcaagc agatttatcg ccagcagctc cgaatagcgc 540
ccttcccctt gcccggcgtt aatgatttgc ccaaacaggt cgctgaaatg cggctggtgc 600
gcttcatccg ggcgaaagaa ccccgtattg gcaaatattg acggccagtt aagccattca 660
tgccagtagg cgcgcggacg aaagtaaacc cactggtgat accattcgcg agcctccgga 720
tgacgaccgt agtgatgaat ctctcctggc gggaacagca aaatatcacc cggtcggcaa 780
acaaattctc gtccctgatt tttcaccacc ccctgaccgc gaatggtgag attgagaata 840
taacctttca ttcccagcgg tcggtcgata aaaaaatcga gataaccgtt ggcctcaatc 900
ggcgttaaac ccgccaccag atgggcatta aacgagtatc ccggcagcag gggatcattt 960
tgcgcttcag ccatactttt catactcccg ccattcagag aagaaaccaa ttgtccatat 1020
tgcatcagac attgccgtca ctgcgtcttt tactggctct tctcgctaac caaaccggta 1080
accccgctta ttaaaagcat tctgtaacaa agcgggacca aagccatgac aaaaacgcgt 1140
aacaaaagtg tctataatca cggcagaaaa gtccacattg attatttgca cggcgtcaca 1200
ctttgctatg ccatagcatt tttatccata agattagcgg atcctacctg acgcttttta 1260
tcgcaactct ctactgtttc tccatacccg tttttttggg ctagcgaatt caggaggaaa 1320 cg atg agt aac ttc tct gga ttt acg aaa gga acc gat atc gca gac 1367
Met Ser Asn Phe Ser Gly Phe Thr Lys Gly Thr Asp Ile Ala Asp
1 5 10 15 tta gat gcg gtg gct caa acg ctc aag aag cca gca gac gat gca aac 1415
Leu Asp Ala Val Ala Gln Thr Leu Lys Lys Pro Ala Asp Asp Ala Asn
20 25 30 aaa gcg gtt aat gac tcg ata gca gca ttg aaa gat aag cct gac aac 1463
Lys Ala Val Asn Asp Ser Ile Ala Ala Leu Lys Asp Lys Pro Asp Asn
35 40 45 ccg gcg cta ctt gct gac tta caa cat tca att aat aaa tgg tcg gta 1511
Pro Ala Leu Leu Ala Asp Leu Gln His Ser Ile Asn Lys Trp Ser Val -continued

```
        50                  55                  60

att tac aat ata aac tca acc ata gtt cgt agc atg aaa gac tta atg     1559
Ile Tyr Asn Ile Asn Ser Thr Ile Val Arg Ser Met Lys Asp Leu Met
    65                  70                  75

caa ggc atc cta cag aag ttc cca taa ggatcccgcg ggatcctct            1606
Gln Gly Ile Leu Gln Lys Phe Pro
80                  85

agagtcgacc tgcaggcatg caagcttggc tgttttggcg gatgagagaa gattttcagc   1666

ctgatacaga ttaaatcaga acgcagaagc ggtctgataa aacagaattt gcctggcggc   1726

agtagcgcgg tggtcccacc tgaccccatg ccgaactcag aagtgaaacg ccgtagcgcc   1786

gatggtagtg tggggtctcc ccatgcgaga gtagggaact gccaggcatc aaataaaacg   1846

aaaggctcag tcgaaagact gggcctttcg ttttatctgt tgtttgtcgg tgaacgctct   1906

cctgagtagg acaaatccgc cgggagcgga tttgaacgtt gcgaagcaac ggcccggagg   1966

gtggcgggca ggacgcccgc cataaactgc caggcatcaa attaagcaga aggccatcct   2026

gacggatggc ctttttgcgt ttctacaaac tctttttgttt atttttctaa atacattcaa  2086

atatgtatcc gctcatgaga caataaccct gataaatgct tcaataatat tgaaaaagga   2146

agagtatgag tattcaacat ttccgtgtcg cccttattcc cttttttgcg gcattttgcc   2206

ttcctgtttt tgctcaccca gaaacgctgg tgaaagtaaa agatgctgaa gatcagttgg   2266

gtgcacgagt gggttacatc gaactggatc tcaacagcgg taagatcctt gagagttttc   2326

gccccgaaga acgttttcca atgatgagca cttttaaagt tctgctatgt ggcgcggtat   2386

tatcccgtgt tgacgccggg caagagcaac tcggtcgccg catacactat tctcagaatg   2446

acttggttga gtactcacca gtcacagaaa agcatcttac ggatggcatg acagtaagag   2506

aattatgcag tgctgccata accatgagtg ataacactgc ggccaactta cttctgacaa   2566

cgatcggagg accgaaggag ctaaccgctt ttttgcacaa catgggggat catgtaactc   2626

gccttgatcg ttgggaaccg gagctgaatg aagccatacc aaacgacgag cgtgacacca   2686

cgatgcctgc agcaatggca acaacgttgc gcaaactatt aactggcgaa ctacttactc   2746

tagcttcccg gcaacaatta atagactgga tggaggcgga taaagttgca ggaccacttc   2806

tgcgctcggc ccttccggct ggctggttta ttgctgataa atctggagcc ggtgagcgtg   2866

ggtctcgcgg tatcattgca gcactggggc cagatggtaa gccctcccgt atcgtagtta   2926

tctacacgac ggggagtcag gcaactatgg atgaacgaaa tagacagatc gctgagatag   2986

gtgcctcact gattaagcat tggtaactgt cagaccaagt ttactcatat atactttaga   3046

ttgatttacg cgccctgtag cggcgcatta agcgcggcgg gtgtggtggt tacgcgcagc   3106

gtgaccgcta cacttgccag cgccctagcg cccgctcctt tcgctttctt cccttccttt   3166

ctcgccacgt tcgccggctt tccccgtcaa gctctaaatc gggggctccc tttagggttc   3226

cgatttagtg ctttacggca cctcgacccc aaaaaacttg atttgggtga tggttcacgt   3286

agtgggccat cgccctgata gacggttttt cgccctttga cgttggagtc cacgttcttt   3346

aatagtggac tcttgttcca aacttgaaca acactcaacc ctatctcggg ctattctttt   3406

gatttataag ggattttgcc gatttcggcc tattggttaa aaaatgagct gatttaacaa   3466

aaatttaacg cgaattttaa caaaatatta acgtttacaa tttaaaagga tctaggtgaa   3526

gatccttttt gataatctca tgaccaaaat cccttaacgt gagttttcgt tccactgagc   3586

gtcagacccc gtagaaaaga tcaaaggatc ttcttgagat cctttttttc tgcgcgtaat   3646

ctgctgcttg caaacaaaaa aaccaccgct accagcggtg gtttgtttgc cggatcaaga   3706
```

-continued

```
gctaccaact cttttccga aggtaactgg cttcagcaga gcgcagatac caaatactgt   3766
ccttctagtg tagccgtagt taggccacca cttcaagaac tctgtagcac cgcctacata   3826
cctcgctctg ctaatcctgt taccagtggc tgctgccagt ggcgataagt cgtgtcttac   3886
cgggttggac tcaagacgat agttaccgga taaggcgcag cggtcgggct gaacgggggg   3946
ttcgtgcaca cagcccagct tggagcgaac gacctacacc gaactgagat acctacagcg   4006
tgagctatga gaaagcgcca cgcttcccga agggagaaag gcggacaggt atccggtaag   4066
cggcagggtc ggaacaggag agcgcacgag ggagcttcca gggggaaacg cctggtatct   4126
ttatagtcct gtcgggtttc gccacctctg acttgagcgt cgatttttgt gatgctcgtc   4186
aggggggcgg agcctatgga aaaacgccag caacgcggcc tttttacggt tcctggcctt   4246
ttgctggcct tttgctcaca tgttctttcc tgcgttatcc cctgattctg tggataaccg   4306
tattaccgcc tttgagtgag ctgataccgc tcgccgcagc cgaacgaccg agcgcagcga   4366
gtcagtgagc gaggaagcgg aagagcgcct gatgcggtat tttctcctta cgcatctgtg   4426
cggtatttca caccgcatat ggtgcactct cagtacaatc tgctctgatg ccgcatagtt   4486
aagccagtat acactccgct atcgctacgt gactgggtca tggctgcgcc ccgacacccg   4546
ccaacacccg ctgacgcgcc ctgacgggct tgtctgctcc cggcatccgc ttacagacaa   4606
gctgtgaccg tctccgggag ctgcatgtgt cagaggtttt caccgtcatc accgaaacgc   4666
gcgaggcagc aaggagatgg cgcccaacag tcccccggcc acggggcctg ccaccatacc   4726
cacgccgaaa caagcgctca tgagcccgaa gtggcgagcc cgatcttccc catcggtgat   4786
gtcggcgata taggcgccag caaccgcacc tgtggcgccg gtgatgccgg ccacgatgcg   4846
tccggcgtag aggatctgct catgtttgac agcttatc                           4884
```